US008206910B2

(12) United States Patent
Eng

(10) Patent No.: US 8,206,910 B2
(45) Date of Patent: Jun. 26, 2012

(54) TARGETS FOR USE IN DIAGNOSIS, PROGNOSIS AND THERAPY OF BREAST CANCER

(75) Inventor: Charis Eng, Cleveland Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 12/633,539

(22) Filed: Dec. 8, 2009

(65) Prior Publication Data

US 2010/0159466 A1 Jun. 24, 2010

Related U.S. Application Data

(60) Provisional application No. 61/201,156, filed on Dec. 8, 2008.

(51) Int. Cl.
*C12P 19/34* (2006.01)
*C12Q 1/68* (2006.01)
(52) U.S. Cl. .......... 435/6.1; 435/6.14; 435/91.2; 436/64
(58) Field of Classification Search ........................ None
See application file for complete search history.

(56) References Cited

U.S. PATENT DOCUMENTS

| 2003/0165895 | A1 | 9/2003 | Czerniak et al. |
| 2010/0092961 | A1 | 4/2010 | Eng |
| 2010/0255478 | A1 | 10/2010 | Eng |
| 2011/0014603 | A1 | 1/2011 | Eng et al. |

FOREIGN PATENT DOCUMENTS

| WO | WO 2005/078139 A | 8/2005 |
| WO | WO 2005/118806 A | 12/2005 |
| WO | WO 2006/028967 A | 3/2006 |
| WO | WO 2008/002672 | 1/2008 |

OTHER PUBLICATIONS

Pepe (Am J Epid, 2004, vol. 159, No. 9, pp. 882-890).*
Lucentini et al (The Scientist (2004) vol. 18, p. 20).*
Wacholder et al (J. Natl. Cancer Institute (2004) 96(6):434-442).*
Hirschhorn et al. (Genetics in Medicine. vol. 4, No. 2, pp. 45-61, Mar. 2002).*
Halushka (Nature. Jul. 1999. 22: 239-247).*
6th edition of the American Joint Committee on Cancer (AJCC) Cancer Staging Manual (Greene, F., et al., eds. AJCC Cancer Staging Manual, 6th edition. New York: Springer-Verlag; (2002)).
A Conference on Nonparametric Inference and Probability with Applications to Science (Honoring Michael Woodroofe), Ann Arbor, Michigan, 2005). The R package (http://www.r-project.org).
Ada-Nguema, A. S., et al., "The Small GTPase R-Ras Regulates Organization of Actin and Drives Membrane Protrusions Through the Activity of PLCε," *Journal of Cell Science*, 119:1307-1319 (2006).
Aldred, M.A., et al., "Papillary and Follicular Thyroid Carcinomas Show Distinctly Different Microarray Expression Profiles and can be Distinguished by a Minimum of Five Genes," *J Clin Onco.* 22(17):3531-3539 (2004).

Aldred, M.A., et al., "Peroxisome Proliferator-activated Receptor Gamma is Frequently Downregulated in a Diversity of Sporadic Nonmedullary Thyroid Carcinomas," *Oncogen* 22:3412-3416 (2003).
Allinen, M., et al., "Molecular Characterization of the Tumor Microenvironment in Breast Cancer," *Cancer Cell* 6:17-32 (2004).
Alvarez-Garcia, I., et al., "MicroRNA Functions in Animal Development and Human Disease," *Development* 132(21):4653-4662 (2005).
Antoniou, A. C., et al., "A Comprehensive Model for Familial Breast Cancer Incorporating BRCA1, BRCA2 and Other Genes," *British Journal of Cancer*, 86:76-83 (2002).
Appelhoff, R.J., et al., "Differential Function of the Prolyl Hydorxylases PHD1, PHD2, and PHD3 in the Regulation of Hypoxia-inducible Factor," *J of Bio Chem* 279(37):38458-38465 (2004).
Argraves, W.S., et al., "Fibulins: Physiological and Disease Perspectives," *EMBO Reports* 4(12):1127-1131 (2003).
Auer, H., et al., "Chipping Away at the Chip Bias: RNA Degradation in Microarray Analysis," *Nature Genetics* 35(4):292-293 (2003).
Barclay, W. W., et al., "A System for Studying Epithelial-Stromal Interactions Reveals Distinct Inductive Abilities of Stromal Cells from Benign Prostatic Hyperplasia and Prostate Cancer," *Endocrinology*, 146(1):13-18 (Jan. 2005).
Baysal, B.E., et al., "Mutations in *SDHD*, a Mitochondrial Complex II Gene, in Hereditary Paraganglioma," *Science*, 287:848-851 (Feb. 4, 2000).
Benn, D.E., et al., "Clinical Presentation and Penetrance of Pheochromocytoma/Paraganglioma Syndromes," *The Journal of Clinical Endocrinology & Metabolism*, 91(3): 827-836 (2006; Online Nov. 29, 2005).
Berezikov, E., et al., "Approaches to MicroRNA Discovery," *Nature Genetics* 38:S2-S7 (2006).
Bhowmick, N. A., et al., "Stromal Fibroblasts in Cancer Initiation and Progression," *Nature* 432:332-337 (2004).
Bissell, M.J., et al., "The Influence of Extracellular Matrix on Gene Expression: Is Structure the Message?," *J. Cell Sci. Suppl* 8:327-343 (1987).
Bockmühl, U., et al., "Chromosomal Alterations During Metastasis Formation of Head and Neck Squamous Cell Carcinoma," *Genes, Chromosomes & Cancers* 33:29-35 (2002).
Bockmühl, U., MD, et al., "Genomic Alterations Associated with Malignancy in Head and Neck Cancer," *Head & Neck* 20:145-151 (1998).
Bonneau, D., et al., "Mutations of the Human PTEN Gene," *Human Mutation* 16:109-122 (2000).
Boucheix, C., et al., "Tetraspanins and Malignancy," *Expert Reviews in Molecular Medicine*:1-17 (2001).
Braakhuis, B.J.M., et al., "A Genetic Explanation of Slaughter's Concept of Field Cancerization: Evidence and Clinical Implications," *Cancer Research* 63:1727-1730 (2003).

(Continued)

*Primary Examiner* — Sarae Bausch
(74) *Attorney, Agent, or Firm* — Hamilton, Brook, Smith & Reynolds, P.C.

(57) ABSTRACT

The invention is directed to methods of diagnosing breast cancer, susceptibility to breast cancer, nodal metastasis of a breast cancer and screening for breast cancer in an individual in need thereof comprising detecting the presence of a loss of heterozygosity/allelic imbalance (LOH/AI) at one or more specific loci (markers) in the genome of the individual, wherein the presence of the LOH/AI at the one or more specific loci in the genome of the individual is indicative of a diagnosis of breast cancer in the individual.

13 Claims, 3 Drawing Sheets

OTHER PUBLICATIONS

Braakhuis, B.J.M., et al., "Expanding Fields of Genetically Altered Cells in Head and Neck Squamous Carcinogenesis," *Seminars in Cancer Biology 15*:113-120 (2005).

Calin, G.A., MD, PhD, et al., "A MicroRNA Signature Associated with Prognosis and Progression in Chronic Lymphocytic Leukemia," *N Engl J Med 353*(17):1793-1801 (2005).

Canobbio, I., et al., "Altered Cytoskeleton Organization in Platelets from Patients with MYH9-related Disease," *J of Thrombosis and Haemostasis 3*:1026-1035 (2005).

Carethers, J.M., et al., "Absence of *PTEN/MMAC1* Germ-Line Mutations in Sporadic Bannayan Riley-Ruvalcaba Syndrome," *Cancer Research 58*:2724-2726 (1998).

Cascon, A., et al., "G12S and H50R Variations are Polymorphisms in the *SDHD* Gene," *Genes, Chromosomes & Cancer*, 37:220-221 (2003).

Cerutti, J.M., et al., "A Preoperative Diagnostic Test that Distinguishes Benign from Malignant Thyroid Carcinoma Based on Gene Expression," *The Journal of Clinical Investigation 113*(8):1234-1242 (2004).

Chen, C.-Z., Ph.D., "MicroRNAs as Oncogenes and Tumor Suppressors," *N Engl J Med 353*:1768-1771 (2005).

Chen, E.I., et al., "Maspin and Tumor Metastasis," *IUBMB Life 58*(1):25-29 (2006).

Chen, S.-L., et al., "p53 is a Regulator of the Metastasis Suppressor Gene Nm23-H1," *Molecular Carcinogenesis*, 36:204-214 (2003).

Chung, J.-H., et al., "Nuclear-Cytoplasmic Partitioning of Phosphatase and Tensin Homologue Deleted on Chromosome 10 (PTEN) Differentially Regulates the Cell Cycle and Apoptosis," *Cancer Res.*, 65(18):8096-8100 (Sep. 15, 2005).

Climent, J., et al., "Genomic Loss of 18p Predicts an Adverse Clinical Outcome in Patients with High-Risk Breast Cancer," *Clinical Cancer Research 8*:3863-3869 (2002).

Cocco, L., et al., "Nuclear Phospholipase C β1, Regulation of the Cell Cycle and Progression of Acute Myeloid Leukemia," *Advan. Enzyme Regul 45*:126-135 (2005).

Condon, M.S., "The Role of the Stromal Microenvironment in Prostate Cancer," *Seminars in Cancer Biology 15*:132-137 (2005).

Cornélis, F., et al., "New Susceptibility Locus for Rheumatoid Arthritis Suggested by a Genome-Wide-Linkage Study," *Proc. Natl. Acad. Sci. USA 95*:10746-10750 (1998).

Cunco, A., et al., "Acquired Chromosome 11q Deletion Involving the Ataxia Teleangiectasia Locus in B-Cell Non-Hodgkin's Lymphoma: Correlation with Clinicobiologic Features," *J of Clin Oncology 18*(13):2607-2614 (2000).

Dacic, S., MD, et al., "Patterns of Allelic Loss of Synchronous Adenocarcinomas of the Lung," *Am J Surg Pathol 29*(7):897-902 (2005).

Dai, M.-S., et al., "The Effects of the Fanconi Anemia Zinc Finger (FAZF) on Cell Cycle, Apoptosis, and Proliferation are Differentiation Stage-specific," *The J. of Biological Chem 277*(29):26327-26334 (2002).

Debies, M.T., et al., "Genetic Basis of Human Breast Cancer Metastasis," *J of Mammary Gland Biology and Neoplasia 6*(4):441-451 (2001).

Denison, S.R., et al., "Characterization of FRA6E and Its Potential Role in Autosomal Recessive Juvenile Parkinsonism and Ovarian Cancer," *Genes, Chromosomes & Cancer 38*:40-52 (2003).

Drysdale, C.M., et al., "Complex Promoter and Coding Region $β_2$-adrenergic Receptor Haplotypes Alter Receptor Expression and Predict in vivo Responsiveness," *PNAS 97*(19):10483-10488 (2000).

Edlund, M., et al., "Modulation of Prostate Cancer Growth in Bone Microenvironments," *Journal of Cellular Biochemistry 91*:686-705 (2004).

Eissa, S., et al., "Multivariate Analysis of DNA ploidy, P53, c-erbB-2 Proteins, EGFR, and Steroid Hormone Receptors for Short Term Prognosis in Breast Cancer," *Anticancer Research*, 17(4B) :3091-3098 (Jul.-Aug. 1997).

Ellsworth, R.E., et al., "Allelic Imbalance in Primary Breast Carcinomas and Metastatic Tumors of the Axillary Lymph Nodes," *Molecular Cancer Research 3* (2):71-77 (2005).

Eng, C., "*PTEN*: One Gene, Many Syndromes," *Human Mutation*, 22:183-198 (2003).

Eng, C., "Will the Real Cowden Syndrome Please Stand Up: Revised Diagnostic Criteria," *J Med Genet 37*:828-830 (2000).

Eng, C., et al., "A Role for Mitochondrial Enzymes in Inherited Neoplasia and Beyond," *Nature Reviews Cancer*, 3:193-202 (Mar. 2003).

Fagin, J.A., "Perspective: Lessons Learned from Molecular Genetic Studies of Thyroid Cancer-Insights into Pathogenesis and Tumor-Specific Therapeutic Targets," *Endocrinology 143*(6):2025-2028 (2002).

Farahati, J., et al., "Changing Trends of Incidence and Prognosis of Thyroid Carcinoma in Lower Franconia, Germany, from 1981-1995," *Thyroid 14*(2):141-147 (2004).

Forastiere, A., M.D., et al., "Head and Neck Cancer," *N. Engl J Med 345*(26):1890-1900 (2001).

Fukino, K., et al., "Combined Total Genome Loss of Heterozygosity Scan of Breast Cancer Stroma and Epithelium Reveals Multiplicity of Stromal Targets," *Cancer Research 64*:7231-7236 (2004).

Fukino, K., et al., "Genomic Instability Within Tumor Stroma and Clinicopathological Characteristics of Sporadic Primary Invasive Breast Carcinoma," *JAMA 297*(19):2103-2111 (2007).

Gallagher, W.M., et al., "Human Fibulin-4: Analysis of its Biosynthetic Processing and mRNA Expression in Normal and Tumour Tissues," *FEBS Letters 489*:59-66 (2001).

Gasco, M., et al., "TP53 Mutations in Familial Breast Cancer: Functional Aspects," *Human Mutation*, 21:301-306 (2003).

Ginzinger, D.G., et al., "Measurement of DNA Copy Number at Microsatellite Loci Using Quantitative PCR Analysis," *Cancer Research 60*:5405-5409 (2000).

Gort, M., et al., "Improvement of Best Practice in Early Breast Cancer: Actionable Surgeon and Hospital Factors," *Breast Cancer Res Treat 102*:219-226 (2007).

Götte, K., et al., "Intratumoral Genomic Heterogeneity in Advanced Head and Neck Cancer Detected by Comparative Genomic Hybridization," *Current Research in Head and Neck Cancer 62*:38-48 (2005).

Greenwood, T.A., et al., "Promoter and Intronic Variants Affect the Transcriptional Regulation of the Human Dopamine Transporter Gene," *Genomics 82*:511-519 (2003).

Grünweller, A., et al., "RNA Interferences as a Gene-Specific Approach for Molecular Medicine," *Current Medicinal Chemistry 12*:3143-3161 (2005).

Haiman, C.A., et al., "Common Genetic Variation at *PTEN* and Risk of Sporadic Breast and Prostate Cancer," *Cancer Epidemiol Biomarkers Prev 15*(5):1021-1025 (2006).

Hainaut, P., and Hollstein, M., "p53 and Human Cancer: The First Ten Thousand Mutations," *Advances in Cancer Research*, 77:81-137 (2000).

Hamilton, J.A., et al., "The Expression Profile for the Tumour Suppressor Gene *PTEN* and Associated Polymorphic Markers," *British Journal of Cancer 82*(10):1671-1676 (2000).

Hartikainen, J.M., et al., "An Autosome-Wide Scan for Linkage Disequilibrium-Based Association in Sporadic Breast Cancer Cases in Eastern Finland: Three Candidate Regions Found," *Cancer Epidemiology, Biomarkers & Prevention 14*(1):75-80 (2005).

Hartman, A.-R., and Ford, J. M., "BRCA1 Induces DNA Damage Recognition Factors and Enhances Nucleotide Excision Repair," *Nature Genetics*, 32:180-184 (Sep. 2002).

Hayward, S. W., et al., "Malignant Transformation in a Nontumorigenic Human Prostatic Epithelial Cell Line," *Cancer Research*, 61:8135-8142 (Nov. 15, 2001).

He, H., et al., "The Role of MicroRNA Genes in Papillary Thyroid Carcinoma," *PNAS 102*(52):19075-19080 (2005).

Hill, R., et al., "Selective Evolution of Stromal Mesenchyme with p53 Loss in Response to Epithelial Tumorigenesis," *Cell 123*:1001-1011 (2005).

Hoatlin, M.E., et al., "A Novel BTB/POZ Transcriptional Repressor Protein Interacts with the Fanconi Anemia Group C Protein and PLZF," *Blood 94*:3737-3747 (1999).

Hollstein, M., et al., "p53 Mutations in Human Cancers," *Science*, 253:49-53 (Jul. 5, 1991).

Horváth, B., MD, et al., "Expression of ETS-1 Transcription Factor in Human Head and Neck Squamous Cell Carcinoma and Effect of Histamine on Metastatic Potential of Invasive Tumor Through the Regulation of Expression of ETS-1 and Matrix Metalloproteinase-3," *Head & Neck* 27:585-596 (2005).

Hu, M., et al., "Distinct Epigenetic Changes in the Stromal Cells of Breast Cancers," *Nature Genetics* 37(8):899-905 (2005).

Huang, Q., et al.. "Genetic Differences Detected by Comparative Genomic Hybridization in Head and Neck Squamous Cell Carcinomas from Different Tumor Sites: Construction on Oncogenetic Trees for Tumor Progression," *Genes, Chromosomes & Cancer* 34:224-233 (2002).

Hunter, K.D., et al., "Profiling Early Head and Neck Cancer," *Cancer* 5:127-135 (2005).

Hussain, S., et al., "Direct Interaction of FANCD2 with BRCA2 in DNA Damage Response Pathways," *Human Molecular Genetics* 13 (12):1241-1248 (2004).

Iorio, M.V., et al.. "MicroRNA Gene Expression Deregulation in Human Breast Cancer," *Cancer Res* 65(16):7065-7070 (2005).

Ishii, T., et al., "A Mutation in the *SDHC* Gene of Complex II Increases Oxidative Stress, Resulting in Apoptosis and Tumorigenesis," *Cancer Res.*, 65(1):203-209 (Jan. 1, 2005).

Jang, S.J., et al., "Multiple Oral Squamous Epithelial Lesions: Are They Genetically Related?," *Oncogene* 20:2235-2242 (2001).

Jiang, J., et al., "Real-time Expression Profiling of microRNA Precursors in Human Cancer Cell Lines", *Nucleic Acids Res.*, 33(17):5394-5403 (2005).

Jukkola, T., et al., "*Drapc1*Expression During Mouse Embryonic Development," *Gene Expression Patterns* 4:755-762 (2004).

Kastan, M. B., and Bartek, J., "Cell-Cycle Checkpoints and Cancer," *Nature*, 432:316-323 (Nov. 18, 2004).

Kebebew, E., MD, "Diagnostic and Prognostic Value of Angiogenesis-Modulating Genes in Malignant Thyroid Neoplasms," *Surgery* 138:1102-1110 (2005).

Khanna, K.K., et al., "ATM and Genome Maintenance: Defining Its Role in Breast Cancer Susceptibility," *J. of Mammary Gland Biology and Neoplasia* 9(3):247-262 (2004).

Kimura, E.T., et al., "High Prevalence of *BRAF*Mutations in Thyroid Cancer: Genetic Evidence for Constitutive Activation of the RET/PTC-RAS-BRAF Signaling Pathway in Papillary Thyroid Carcinoma," *Cancer Research* 63:1454-1457 (2003).

Kleinjan, D.A., et al., "Long-Range Control of Gene Expression: Emerging Mechanisms and Disruption in Disease," *Am. J. Hum. Genet.* 76:8-32 (2005).

Koivunen, P., et al., "Inhibition of Hypoxia-inducible Factor (HIF) Hydroxylases by Citric Acid Cycle Intermediates Possible Links Between Cell Metabolism and Stabilization of HIF," *The Journal of Biological Chemistry*, 282(7):4524-4532 (Feb. 16, 2007).

Kraiem, Z., et al., "Matrix Metalloproteinases and the Thyroid," *Thyroid* 10(12):1061-1069 (2000).

Krubasik, D., et al., "Absence of p300 Induces Cellular Phenotypic Changes Characteristic of Epithelial to Mesenchyme Transition," *British Journal of Cancer* 94:1326-1332 (2006).

Krützfeldt, J., et al., "Silencing of microRNAs in vivo with 'antagomirs'," *Nature* 438:685-689 (2005).

Kryukov, G.V., et al., "Most Rare Misense Alleles are Deleterious in Humans: Implications for Complex Disease and Association Studies," *The American Journal of Human Genetics*, 80:727-739 (Apr. 2007).

Kurose, K., et al., "Frequent Somatic Mutations in *PTEN* and *TP53* are Mutually Exclusive in the Stroma of Breast Carcinomas," *Nature Genetics* 32:355-357 (2002).

Kurose, K., et al., "Genetic Model of Multi-Step Breast Carcinogenesis Involving the Epithelium and Stroma: Clues to Tumour-Microenvironment Interactions," *Human Molecular Genetics* 10(18):1907-1913 (2001).

Kurose, K., et a., "Frequent Somatic Mutations in PTEN and TP53are Mutually Exclusive in the Stroma of Breast Carcinomas," *Nature Genetics*, 32:681 (Dec. 2002).

Kytölä, S., et al., "Alterations of the *SDHD* Gene Locus in Midgut Carcinoids, Merkel Cell Carcinomas, Pheochromocytomas, and Abdominal Paragangliomas," *Genes, Chromosomes & Cancer*, 34:325-332 (2002).

Lagos-Quintana, M., et al., "New MicroRNAs from Mouse and Human," *RNA* 9:175-179 (2003).

Launonen, V., et al., "Inherited Susceptibility to Uterine Leiomyomas and Renal Cell Cancer," *PNAS*, 98(6):3387-3392 (Mar. 13, 2001).

Lee, S.-R., et al., "Reversible Inactivation of the Tumor Suppressor PTEN by $H_2O_2$," *The Journal of Biochemical Chemistry* 277(23):20336-20342 (Jun. 7, 2002).

Leng, K., et al., "Refined Characterization of Head and Neck Squamous Cell Carcinomas Expressing a Seemingly Wild-type p53 Protein," *J Oral Pathol Med* 35:19-24 (2006).

Liaw, D., et al., "Germline Mutations of the *PTEN* Gene in Cowden Disease, an Inherited Breast and Thyroid Cancer Syndrome," *Nature Genetics*, 16:64-67 (May 1997).

Liu, C.-G., et al., "An Oligonucleotide Microchip for Genome-wide MicroRNA Profiling in Human and Mouse Tissues," *PNAS* 101(26):9740-9744 (2004).

Loffeld, A., et al., "Epidermal Naevus in Proteus Syndrome Showing Loss of Heterozygosity for an Inherited PTEN Mutation," *British Journal of Dermatology* 154:1194-1198 (2006).

Lu, J., et al., "MicroRNA Expression Profiles Classify Human Cancers," *Nature* 435:834-838 (2005).

Maehama, T., et al., "The Tumor Suppressor, PTEN/MMAC1, Dephosphorylates the Lipid Second Messenger, Phosphatidylinositol 3,4,5-Trisphosphate," *The Journal of Biological Chemistry* 273(22):13375-13378 (1998).

Maffini, M. V., et al., "Stromal Regulation of Neoplastic Development: Age-Dependent Normalization of Neoplastic Mammary Cells by Mammary Stroma," *American Journal of Pathology* 167(5):1405-1410 (Nov. 2005).

Marsh, D.J., et al., "Differential Loss of Heterozygosity in the Region of the Cowden Locus Within 10q22-23 in Follicular Thyroid Adenomas and Carcinomas," *Cancer Research* 57:500-503 (1997).

Marsh, D.J., et al., "Mutation Spectrum and Genotype-phenotype Analyses in Cowden Disease and Bannayan-Zonana Syndrome, Two Hamartoma Syndromes with Germline *PTEN* Mutation," *Human Molecular Genetics*, 7(3):507-515 (1998).

Marsh, D.J., et al., "*PTEN* Mutation Spectrum and Genotype-Phenotype Correlations in Bannayan-Riley-Ruvalcaba Syndrome Suggest a Single Entity with Cowden Syndrome," *Human Molecular Genetics* 8(8): 1461 -1472 (1999).

Martin, A.-M., et al., "Germline *TP53* Mutations in Breast Cancer Families with Multiple Primary Cancers: Is *TP53* a Modifier of *BRCA1?*," *J. Med. Genet.*, 40(/e34):1-6 (2003).

Matrisian, L. M., et al., "Epithelial-Stromal Interactions and Tumor Progression: Meeting Summary and Future Directions," *Cancer Research*, 61:3844-3846 (May 1, 2001).

McCawley, L.J., et al., "Tumor Progression: Defining the Soil Round the Tumor Seed," *Current Biology* 11:R25-R27 (2001).

McWhinney, S.R., et al., "Large Germline Deletions of Mitochondrial Complex II Subunits *SDHB* and *SDHB* in Hereditary Paraganglioma," *The Journal of Clinical Endocrinology & Metabolism*, 89(11):5694-5699 (2004).

Miska, E.A., "How MicroRNAS Control Cell Division, Differentiation and Death," *Current Opinion in Genetics & Development* 15:563-568 (2005).

Moinfar, F., et al., "Concurrent and Independent Genetic Alterations in the Stromal and Epithelial Cells of Mammary Carcinoma: Implications for Tumorigenesis," *Cancer Research* 60:2562-2566 (2000).

Mueller, M.M., et al., "Friends or Foes—Bipolar Effects of the Tumour Stroma in Cancer," *Cancer* 4:839-849 (2004).

Murakami, Y., et al., "Comprehensive Analysis of MicroRNA Expression Patterns in Hepatocellular Carcinoma and Non-Tumorous Tissues," *Oncogene* 25:2537-2545 (2006).

Mutter, G.L., et al., "Altered PTEN Expression as a Diagnostic Marker for the Earliest Endometrial Precancers," *Journal of National Cancer Institute*, 92(11):924-931 (Jun. 7, 2000).

Naguibneva, I., et al., "The MicroRNA *miR*-181 Targets the Homeobox Protein Hox-A11 During Mammalian Myoblast Differentiation," *Nature Cell Biology* 8(3):278-284 (2006).

Narod, S. A., and Foulkes, W. D., "BRCA1 and BRCA2: 1994 and Beyond," *Nature*, 4:665-676 (Sep. 2004).

Nelen, M.R., et al., "Localization of the Gene for Cowden Disease to Chromosome 10q22-23," *Nature Genetics*, 13:114-116 (May 1996).

Nelson, H.H., et al., "*TP53* Mutation, Allelism and Survival in Non-small Cell Lung Cancer," *Carcinogenesis* 26(10):1770-1773 (2005).

Neumann, H.P.H., et al., "Germ-line Mutations in Nonsyndromic Pheochromocytoma," *N. Engl. J. Med.*, 346(19):1459-1466 (May 9, 2002).

Ni, Y., et al., "Germline Mutations and Variants in the Succinate Dehydrogenase Genes in Cowden and Cowden-like Syndromes," *The American Journal of Human Genetics*, 83:261-268 (Aug. 8, 2008).

Nigro, J.M., et al, "Technical Advance Detection of 1p and 19q Loss in Oligodendroglioma by Quantitative Microsatellite Analysis, a Real-Time Quantitative Polymerase Chain Reaction Assay," *American Journal of Pathology 158*(4):1253-1262 (2001).

Non-published U.S. Appl. No. 12/462,053, filed Jul. 27, 2009.

Overgaard, J., et al., "*TP53* Mutation is an Independent Prognostic Marker for Poor Outcome in Both Node-negative and Node-positive Breast Cancer," *Acta Oncologica 39*:(3)327-333 (2000).

Passler, C., et al., "Prognostic Factors of Papillary and Follicular Thyroid Cancer: Differences in an Iodine-Replete Endemic Goiter Region," *Endocrine-Related Cancer 11*:131-139 (2004).

Patocs, A., et al., "Breast-Cancer Stromal Cells with *TP53* Mutations and Nodal Metastases," *The New England Journal of Medicine.*, 357(25):2543-2551 (Dec. 20, 2007).

Perez-Ordoñez, B., et al., "Molecular Biology of Squamous Cell Carcinoma of the Head and Neck," *J Clin Pathol 59*:445-453 (2006).

Perren, A., et al., "Absence of Somatic *SDHD* Mutations in Sporadic Neuroendocrine Tumors and Detection of Two Germline Variants in Paraganglioma Patients," *Oncogene*, 21:7605-7608 (2002).

Pharoah, P. D. P., et al., "Somatic Mutations in the *p53* Gene and Prognosis in Breast Cancer: A Meta-Analysis," *British Journal of Cancer*, 80(12):1968-1973 (1999).

Pilarski, R., et al., "Will the Real Cowen Syndrome Please Stand Up (Again)? Expanding Mutational and Clinical Spectra of the *PTEN* Hamartoma Tumour Syndrome," *J Med Genet 41*:323-326 (2004).

Poy, M.N., et al., "A Pancreatic Islet-Specific MicroRNA Regulates Insulin Secretion," *Nature 432*:226-230 (2004).

Radmacher, M.D., et al., "A Paradigm for Class Prediction Using Gene Expression Profiles," *Journal of Computational Biology 9*(3):505-511 (2002).

Ricci, F., et al., "Stromal Responses to Carcinomas of the Pancreas," *Cancer Biology & Therapy 4*(3):302-307 (2005).

Ries, L.A.G., et al., "Surveillance Epidemiology and End Results," *Cancer Statistics Review National Cancer Institute* 1975-2003 (2006).

Rio, P.G., et al., "Loss of Heterozygosity of BRCA1, BRCA2 and ATM Genes in Sporadic Invasive Ductal Breast Carcinoma," *International Journal of Oncology 13*:849-853 (1998).

Rosenquist, T.A., et al., "The Novel DNA Glycosylase, NEIL1, Protects Mammalian Cells from Radiation-mediated Cell Death," *DNA Repair 2*:581-591 (2003).

Rosenthal, E., et al., "Elevated Expression of TGF-β1 in Head and Neck Cancer-Associated Fibroblasts," *Molecular Carcinogenesis 40*:116-121 (2004).

Sarquis, M.S., et al., "High Frequency of Loss of Heterozygosity in Imprinted, Compared with Nonimprinted, Genomic Regions in Follicular Thyroid Carcinomas and Atypical Adenomas," *The Journal of Clinical Endocrinology & Metabolism 91*(1):262-269 (2006).

Schedin, P., et al., "Multistep Tumorigenesis and the Microenvironment," *Breast Cancer Res 6*:93-101 (2004).

Schulte, K.-M., et al., "Activin A and Activin Receptors in the Human Thyroid: A Link to the Female Predominance of Goiter?," *Horm Metab Res 32*:390-400 (2000).

Schulte, K.-M., et al, "Activin A and Activin Receptors in Thyroid Cancer," *Thyroid 11*(1):3-14 (2001).

Segev, D.L., et al., "Molecular Pathogenesis of Thyroid Cancer," *Surgical Oncology 12*:69-90 (2003).

Segev, D.L., M.D., et al., "Beyond the Suspicious Thyroid Fine Needle Aspirate A Review," *Acta Cytol 47*:709-722 (2003).

Sclak, M.A., et al., "Succinate Links TCA Cycle Dysfunction to Oncogenesis by Inhibiting HIF-αProlyl Hydroxylase," *Cancer Cell*, 7:77-85 (Jan. 2005).

Shekhar, M.P.V., et al., "Breast Stroma Plays a Dominant Regulatory Role in Breast Epithelial Growth and Differentiation: Implications for Tumor Development and Progression," *Cancer Research 61*:1320-1326 (2001).

Shiozawa, S., et al., "Identification of the Gene Loci that Predispose to Rheumatoid Arthritis," *International Immunology 10*(12):1891-1895 (1998).

Simpson, P.T., et al., "Molecular Evolution of Breast Cancer," *J Pathol 205*:248-254 (2005).

Slager, S.L., et al., "Confirmation of Linkage of Prostate Cancer Aggressiveness with Chromosome 19q," *Am. J. Hum. Genet. 72*:759-762 (2003).

Slane, B.G., et al., "Mutation of Succinate Dehydrogenase Subunit C Results in Increased $O_2$ Oxidative Stress, and Genomic Instability," *Cancer Res.*, 66(15):7615-7620 (Aug. 1, 2006).

Slaughter, D.P., et al., "'Field Cancerizatian' in Oral Stratified Squamous Epithelium Clinical Implications of Multicentric Origin," *Cancer 6*:963-8 (1953).

Smith, J.M., et al., "Germline Mutation of the Tumour Suppressor *PTEN*in Proteus Syndrome," *J Med Genet 39*:937-940 (2002).

Smith, P. D., et al., "Novel p53 Mutants Selected in BRCA-Associated Tumours Which Dissociate Transformation Suppression from Other Wild-type p53 Functions," *Oncogene*, 18:2451-2459 (1999).

Stambolic, V., et al., "High Incidence of Breast and Endometrial Neoplasia Resembling Human Cowden Syndrome in *pten* $^{+/-}$ Mice," *Cancer Research*, 60:3605-3611 (Jul. 1, 2000).

Stambolic, V., et al., "Negative Regulation of PKB/Akt-Dependent Cell Survival by the Tumor Suppressor PTEN," *Cell*, 95:29-39 (Oct. 2, 1998).

Tang, Y. and Eng, C., "PTEN Autoregulates Its Expression by Stabilization of p53 in a Phosphatase-Independent Manner," *Cancer Research*, 66(2):736-742 (Jan. 15, 2006).

Taniguchi, T., et al., "S-Phase-Specific Interaction of the Fanconi Anemia Protein, FANCD2, with BRCA1 and RAD51," *Blood 100*(7):2414-2420 (2002).

Tran, Y., et al., "Novel Regions of Allelic Deletion on Chromosome 18p in Tumors of the Lung, Brain and Breast," *Oncogene 17*:3499-3505 (1998).

Tuhkanen, H., et al., "Genetic Alterations in the Peritumoral Stromal Cells of Malignant and Borderline Epithelial Ovarian Tumors as Indicated by Allelic Imbalance on Chromosome 3P," *Int. J. Cancer 109*:247-252 (2004).

Umbricht, C.B., et al., "Human Telomerase Reverse Transcriptase Gene Expression and the Surgical Management of Suspicious Thyroid Tumors," *Clinical Cancer Research 10*:5762-5768 (2004).

van Oijen, M.G.C.T., et al., "Oral Field Characterization: Carcinogen-induced Independent Events or Micrometastatic Deposits," *Cancer Epidemiology, Biomarkers & Prevention 9*:249-256 (2000).

Vanharanta, S., et al., "Early-Onset Renal Cell Carcinoma as a Novel Extraparaganglial Component of *SDHB*-Associated Heritable Paraganglioma," *Am. J. Hum. Genet.*, 74:153-159 (2004; electronically Dec. 18, 2003).

Volinia, S., et al., "A MicroRNA Expression Signature of Human Solid Tumors Defines Cancer Gene Targets," *Proceedings of the National Academy of Sciences SA 103*(7):2257-2261 (2006).

Wang, X., et al., "p63 Expression in Normal, Hyperplastic and Malignant Breast Tissues," *Breast Cancer*, 9(3):216-219 (Jul. 2002).

Weber, F., et al., "A Limited Set of Human MicroRNA is Deregulated in Follicular Thyroid Carcinoma," *Journal Clinical Endocrinology & Metabolism 91*(9):3584-3591 (2006).

Weber, F., et al., "Gene-expression Profiling in Differentiated Thyroid Cancer—a Viable Strategy for the Practice of Genomic Medicine," *Future Oncol*. 1(4):497-510 (2005).

Weber, F., et al., "Silencing of the Maternally Imprinted Tumor Suppressor *ARHI* Contributes to Follicular Thyroid Carcinogenesis," *The Journal of Clinical Endocrinology & Metabolism 90*(2):1149-1155 (2005).

Weber, F., et al., "Total-Genome Analysis of *BRCA1/2*-Related Invasive Carcinomas of the Breast Identifies Tumor Stroma as Potential Landscaper for Neoplastic Initiation," *The American Journal of Human Genetics 78*:961-972 (2006).

Weber, F., et al., "Variability in Organ-Specific *EGFR* Mutational Spectra in Tumour Epithelium and Stroma may be the Biological Basis for Differential Responses to Tyrosine Kinase Inhibitors," *British Journal of Cancer 92*:1922-1926 (2005).

Weber, F., M.D., et al., "Microenvironmental Genomic Alterations and Clinicopathological Behavior in Head and Neck Squamous Cell Carcinoma," *JAMA* 297(2)187-195 (2007).

Weigelt, B., et al., "No Common Denominator for Breast Cancer Lymph Node Metastasis," *British Journal of Cancer* 93:924-932 (2005).

Weiler, J., et al., "Anti-miRNA Oligonucleotides (AMOs): Ammunition to Target miRNAs Implicated in Human Disease?," *Gene Therapy* 13:496-502 (2006).

Weng, L.-P., et al., "PTEN Blocks Insulin-mediated ETS-2 Phosphorylation Through MAP Kinase, Independently of the Phosphoinositide 3-kinase Pathway," *Human Molecular Genetics*, 11(15):1687-1696 (2002).

Wernert, N., et al., "Presence of Genetic Alterations in Microdissected Stroma of Human Colon and Breast Cancers," *Anticancer Research* 21:2259-2264 (2001).

Williams, H.K., et al., "Molecular Pathogenesis of Oral Squamous Carcinoma," *J. Clin Pathol: Mol Pathol* 53:165-172 (2000).

Witte, J.S., et al., "Genomewide Scan for Prostate Cancer—Aggressiveness Loci," *Am. J. Hum. Genet.* 67:92-99 (2000).

Worsham, M.J., et al., "Fine-Mapping Loss of Gene Architecture at the $CDKN2B$ ($p15^{INK4b}$), $CDKN2A$ ($p14^{ARF}$, $p16^{INK4a}$), and MTAP Genes in Head and Neck Squamous Cell Carcinoma," *Arch Otolaryngol Head Neck Surg.* 132:409-415 (2006).

Yanaihara, N., et al., "Unique MicroRNA Molecular Profiles in Lung Cancer Diagnosis and Prognosis," *Cancer Cell* 9(3): 189-198 (2006).

Yang, W.-W., et al., "E2F6 Negatively Regulates Ultraviolet-Induced Apoptosis via Modulation of BRCA1," *Cell Death and Differentiation*, 14:807-817 (2007).

Yao, T.-P., et al., "Gene Dosage-Dependent Embryonic Development and Proliferation Defects in Mice Lacking the Transcriptional Integrator p300," *Cell* 93:361-372 (1998).

Yeh, M.W., et al., "False-Negative Fine-Needle Aspiration Cytology Results Delay Treatment and Adversely Affect Outcome in Patients with Thyroid Carcinoma," *Thyroid* 14(3):207-215 (2004).

Yu, C., et al., "Functional Haplotypes in the Promoter of Matrix Metalloproteinase-2 Predict Risk of the Occurrence and Metastasis of Esophageal Cancer," *Cancer Research* 64:7622-7628 (2004).

Zbuk, K.M and Eng, C., "Cancer Phenomics: *RET* and *PTEN* as Illustrative Models," *Nature Reviews Cancer*, 7:35-45 (Jan. 2007).

Zeng, Y., et al., "MicroRNAs and Small Interfering RNAs can Inhibit mRNA Expression by Similar Mechanisms," *PNAS* 100(17):9779-9784 (2003).

Zhang, L., et al., "Association of the Phosphatase and Tensin Homolog Gene (PTEN) with Smoking Initiation and Nicotine Dependence," *American Journal of Medical Genetics Part B (Neurophychiatric Genetics)* 141B:10-14 (2006).

Zhou, X.-P., et al., "Association of Germline Mutation in the *PTEN* Tumour Suppressor Gene and Proteus and Proteus-like Syndromes," *The Lancet* 358:210-211 (2001).

Zhou, X.-P., et al., "Germline PTEN Promoter Mutations and Deletions in Cowden/Bannayan-Riley-Ruvalcaba Syndrome Result in Aberrant PTEN Protein and Dysregulation of the Phosphoinositol-3-Kinase/Akt Pathway," *Am. J. Hum. Gener.* 73:404-411 (2003).

Zundel, W., et al., "Loss of *PTEN* Facilitates HIF-1-Mediated Gene Expression," *Genes & Development* 14:391-396 (2000).

Jul. 2, 2008, Notification of Transmittal of the International Search Report and the Written Opinion of the International Searching Authority, or the Declaration, PCT/US2007/015265.

Jan. 15, 2009 Notification Concerning Transmittal of International Preliminary Report on Patentability, PCT/US2007/015265.

Bayley, J.P., "Succinate Dehydrogenase Gene Variants and Their Role in Cowden Syndrome," The American Journal of Human Genetics, 88: 674-675 (2011).

Ni, Y. and Eng, C., "Response to Bayley: Functional Study Informs Bioinformatic Analysis," The American Journal of Human Genetics, 88: 674-676 (2011).

Feb. 24, 2011, Restriction Requirement, U.S. Appl. No. 12/462,053.

Mar. 17, 2011, Restriction Requirement, U.S. Appl. No. 12/343,871.

May 5, 2011, Reply to Restriction Requirement, U.S. Appl. No. 12/343,871.

Jun. 9, 2011, Office Action, U.S. Appl. No. 12/343,871.

Aug. 24, 2011, Reply to Restriction Requirement, U.S. Appl. No. 12/462,053.

Oct. 18, 2011, Office Acton, U.S. Appl. No. 12/462,053.

Dec. 16, 2011, Notice of Allowance, U.S. Appl. No. 12/343,871.

* cited by examiner

TARGETS FOR USE IN DIAGNOSIS, PROGNOSIS AND THERAPY OF BREAST CANCER

RELATED APPLICATIONS

This application claims the benefit of U.S. Provisional Application No. 61/201,156, filed Dec. 8, 2008 and is related to U.S. Provisional Application No. 61/008,007, filed Dec. 18, 2007. The entire teachings of the above applications are incorporated herein by reference.

GOVERNMENT SUPPORT

The invention was supported, in whole or in part, by grants 1P01CA97189-01A2 and 1P50/U54CA113001-01 from the National Cancer Institute. The Government has certain rights in the invention.

BACKGROUND OF THE INVENTION

The importance of cross-talk between a cancer and its microenvironment has been increasingly recognized. A better understanding of this cross-talk would provide improved methods for diagnosis, prognosis and therapy of cancer.

SUMMARY OF THE INVENTION

TP53 mutation analysis and genomewide analysis of loss of heterozygosity and allelic imbalance on DNA from isolated neoplastic epithelial and stromal cells from 43 samples of hereditary breast cancer and 175 samples of sporadic breast cancer were performed. Compartment-specific patterns and TP53 mutations were analyzed. Associations between compartment-specific TP53 status, loss of heterozygosity or allelic imbalance, and clinical and pathological characteristics were computed.

TP53 mutations were associated with an increased loss of heterozygosity and allelic imbalance in both hereditary and sporadic breast cancers, but samples from patients with hereditary disease had more frequent mutations than did those from patients with sporadic tumors (74.4% vs. 42.3%, P=0.001). Only 1 microsatellite locus (2p25.1) in stromal cells from hereditary breast cancers was associated with mutated TP53, whereas there were 66 such loci in cells from sporadic breast cancers. Somatic TP53 mutations in stroma, but not epithelium, of sporadic breast cancers were associated with regional nodal metastases (P=0.003). A specific set of five loci linked to an increased loss of heterozygosity and allelic imbalance in the stroma of sporadic tumors was associated with nodal metastases in the absence of TP53 mutations. No associations were found between any of the clinical or pathological features of hereditary breast cancer with somatic TP53 mutations.

Stroma-specific loss of heterozygosity and allelic imbalance are associated with somatic TP53 mutations and regional lymph-node metastases in sporadic breast cancer but not in hereditary breast cancer.

Accordingly, in one aspect the invention is directed to a method of detecting nodal metastasis of a breast tumor in an individual in need thereof comprising detecting a mutation of the TP53 gene in breast tumor stroma of the individual, a loss of heterozygosity/allelic imbalance (LOH/AI) at one or more loci selected from the group consisting of: D7S821 (7q21), D10S677 (10q23), D15S128 (15Q11), D16S3401 (16p), and D17S2193 (17q24) in breast tumor stroma of the individual, or a combination thereof, wherein the presence of a mutation of the TP53 gene, LOH/AI at the one or more loci, or a combination thereof in the breast tumor stroma indicates nodal metastasis of the breast tumor in the individual.

In another aspect, the invention is directed to a method of diagnosing breast cancer in an individual in need thereof comprising detecting a loss of heterozygosity/allelic imbalance (LOH/AI) at one or more loci selected from the group consisting of: D7S821 (7q21), D10S677 (10q23), D15S128 (15Q11), D16S3401 (16p), and D17S2193 (17q24) in breast tumor stroma of the individual, wherein the LOH/AI at the one or more loci in the breast tumor stroma indicates a diagnosis of breast cancer in the individual. The method can further comprise detecting a mutation of the TP53 gene in breast tumor stroma of the individual.

In yet another aspect, the invention is directed to a kit comprising one or more agents that detect a LOH/AI at one or more loci selected from the group consisting of: D7S821 (7q21), D10S677 (10q23), D15S128 (15q11), D16S3401 (16p), D17S2193 (17q24)) in nucleic acid of an individual. The kit can further comprise one or more agents that detect a mutation in the TP53 gene in the nucleic acid of the individual.

BRIEF DESCRIPTION OF THE DRAWINGS

FIG. 1A shows a comparison of somatic TP53 mutational spectra in epithelium and stroma in sporadic breast cancer and hereditary breast cancer. A representative chromatogram of one sporadic breast cancer shows a GTG173GCG (Val173Ala) mutation of TP53 in stroma but not in epithelium (SEQ ID NOs: 29 and 30). FIG. 1B shows representative immunohistochemical analysis with the use of anti-p53 antibody reveals increased protein expression in tumor stromal fibroblasts of samples with stromal mutant p53 (Gly325Arg) is compared with no expression in the matched normal stroma, which is wild-type p53. FIG. 1C shows sequencing chromatograms for the sporadic breast cancer in Panel B shows a GGA325AGA (Gly325Arg) mutation of TP53 in tumor stroma but not in the matched normal stroma (SEQ ID NOs: 31-34).

DETAILED DESCRIPTION OF THE INVENTION

Figure 1A:
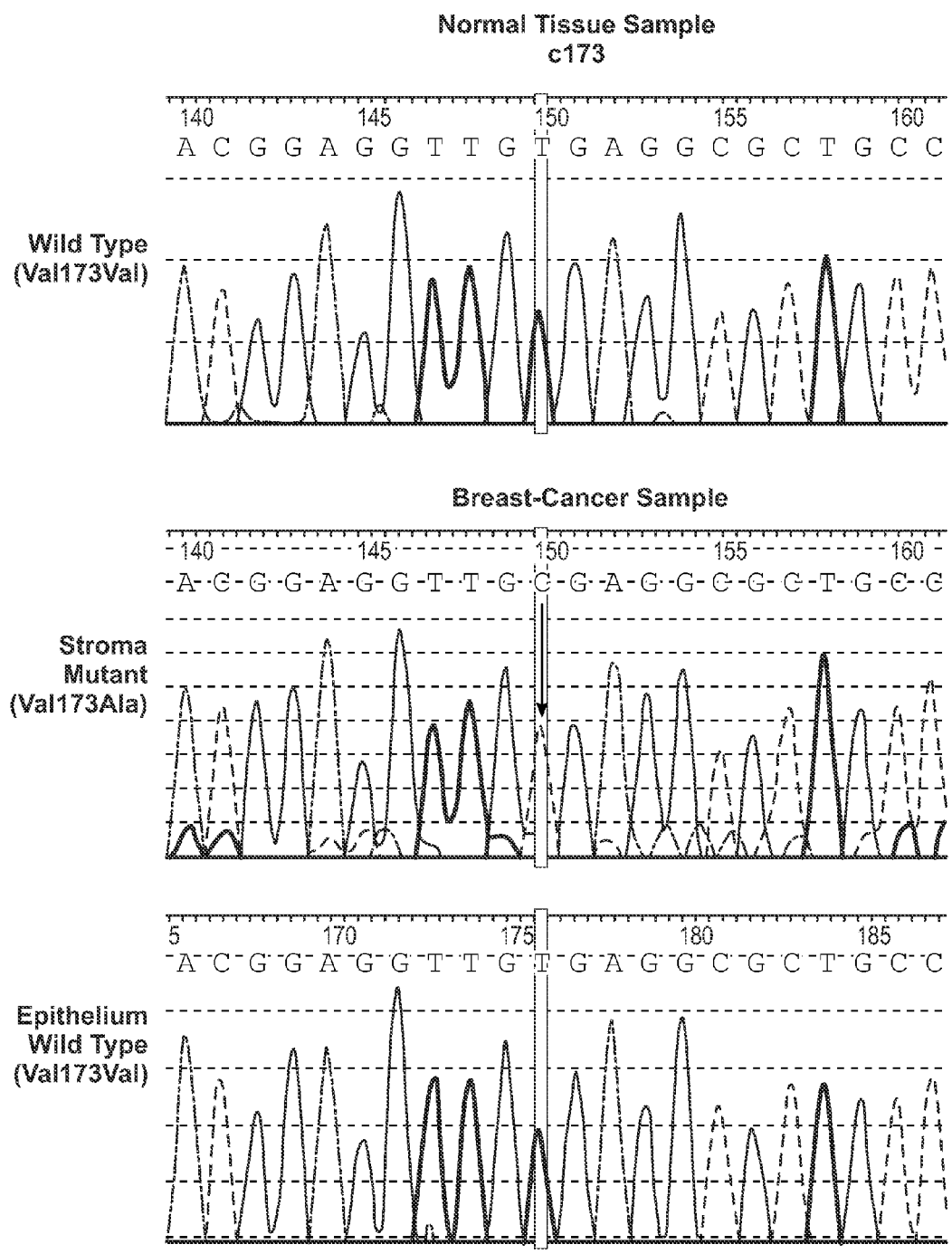
FIGS. 1A-1C show somatic TP53 Mutations in Breast Cancers.

Dynamic interactions between neoplastic epithelial cells and the surrounding stroma can select stromal cells that modulate tumor behavior (Matrisiano L M, et al., *Cancer Res* 2001:61:3844-6; Shekhar M P, et al. *Cancer Res* 2001:61: 1320-6; Bissell M J, et al. *Cell Sci Suppl* 1987:8:527-43.). Moreover, carcinoma-associated stromal cells can transform normal epithelial cells into neoplastic cells (Hayward SW, et al., *Cancer Res* 2001:62:8235-42; Barclay WW, et al., *Endo-* crinology 2005:146:13-8). In an animal model, selective mutations in the reactive stroma of a neoplasm accelerated tumor development, a process that was reversed by stromal gain or loss of certain genes, one of which was TP53 (Hill R, et al., *Cell* 2005:223:1001-11; Maffini M V, et al., *Am J Pathol* 2005:167:1405-10).

Tp53 is the most commonly mutated gene in human neoplasms (Hainaut P, et al., *Adv Cancer Res* 2000:77:71-137). The p53 tumor-suppressor protein involves the cell cycle, checkpoint control, repair of DNA damage, and apoptosis (Hollstein M, et al., *Science* 1991:253:49-53; Kastan M B, Bartek J., *Nature* 2004:432:316-23). In whole-tumor material, the frequency of a TP53 mutation in breast cancers ranges from 20 to 50% and is most common in the hereditary breast-ovarian cancer syndrome that is caused by germline mutations in BRCA1 and BRCA2 (Narod SA, et al., *Nat Rev Cancer* 2004:4:665-76; Antoniou A C, et al., *BR J Cancer* 2002:86:76-83). Like p53, BRCA1 and BRCA2 proteins regulate cell-cycle control and apoptosis (Narod S A, et al., *Nat Rev Cancer* 2004:4:665-76). In vitro work suggests that in cells lacking p53, BRCA1 and BRCA2 upregulate the expression of genes involved in DNA repair (Hartman A R, et al., *Nat Genet* 2002:33:180-4). In BRCA-associated cancers, not only the frequency but also the spectrum of TP53 mutations differ from TP53 mutations in grade-matched sporadic breast cancers (Marun A M, et al., *J Med Genet* 2003:40(4); e34; Gasco M., et al., *Hum Mutat* 2003:21:301-6; Smith P D, et al., *Oncogene* 1999:18:2451-9).

High frequencies of mutations of TP53 and phosphatase and tensin homologue (PTEN) in neoplastic breast epithelium and the surrounding stroma were previously found (Kurose K., et al., *Nat Genet* 2002:32:355-7 (Erratum, Nat Genet 2002:32:681)). In the study of hereditary and sporadic breast cancers described herein, TP53 mutations and loss of heterozygosity and allelic imbalance were sought in neoplastic epithelial cells and surrounding stromal cells and were related to clinical and pathological features of the disease. Shown herein is that mutational inactivation of the tumor-suppressor gene TP53 and genomic alterations in stromal cells of a tumor's microenvironment contribute to the clinical outcome.

Accordingly, in one aspect the invention is directed to methods of diagnosing breast cancer, susceptibility to breast cancer and/or nodal metastasis of a breast cancer in an individual in need thereof comprising detecting a mutation of the TP53 gene, a loss of heterozygosity/allelic imbalance (LOH/AI) at one or more loci or markers (e.g., D7S821 (7q21), D10S677 (10q23), D15S128 (15Q11), D16S3401 (16p), and D17S2193 (17q24)), or a combination thereof in the genome of the individual (e.g., in the breast tumor or the microenvironment of the breast tumor of the individual).

Specifically, in one aspect the invention is directed to methods of diagnosing breast cancer or susceptibility to breast cancer in an individual comprising detecting the presence of a LOH/AI at one or more of five specific loci (D7S821 (7q21), D10S677 (10q23), D15S128 (15q11), D16S3401 (16p), D17S2193 (17q24)) in the genome of the individual, wherein the presence of the LOH/AI at the one or more of five specific loci in the genome of the individual is indicative of a diagnosis of breast cancer in the individual. In one embodiment, the one or more of the loci are present in the stroma (e.g., non-malignant stroma) surrounding a tumor epithelium and/or the epithelium of the tumor. In another embodiment, the presence of one or more of the loci in the stroma surrounding a tumor epithelium and/or the epithelium of the tumor is indicative of nodal metastases. In a particular embodiment, the presence of one or more of the loci in the stroma surrounding a tumor epithelium and/or the epithelium of the tumor is associated with nodal metastases in the absence of one or more TP53 mutations in the tumor stroma. In another embodiment, the presence of one or more of the loci in the stroma surrounding a tumor epithelium and/or the epithelium of the tumor is associated with nodal metastases in the presence of one or more TP53 mutations in the tumor stroma. In this embodiment, the method can further comprise detecting a mutation in the TP53 gene in breast tumor stroma of the individual.

In another aspect the invention is also directed to a method of detecting nodal metastases of a breast cancer (e.g., tumor) in an individual comprising detecting the presence of a LOH/AI at one or more specific loci in the genome of the individual, wherein the presence of the LOH/AI at the one or more specific loci in the genome of the individual is indicative of nodal metastases of a breast cancer in the individual. In one embodiment, the one or more of the loci are present in the stroma surrounding a breast tumor epithelium and/or the epithelium of the tumor. In another embodiment, the presence of one or more of the loci in the stroma surrounding a tumor epithelium and/or the epithelium of the tumor is associated with nodal metastases in the absence of TP53 mutations in the tumor stroma. In another embodiment, the presence of one or more of the loci in the stroma surrounding a tumor epithelium and/or the epithelium of the tumor is associated with nodal metastases in the presence of one or more TP53 mutations in the tumor stroma. In this embodiment, the method can further comprise detecting a mutation in the TP53 gene in breast tumor stroma of the individual. In a particular embodiment, the invention is directed to a method of detecting nodal metastasis of a breast tumor in an individual in need thereof comprising detecting a mutation of the TP53 gene in breast tumor stroma of the individual, a loss of heterozygosity/allelic imbalance (LOH/AI) at one or more loci selected from the group consisting of: D7S821 (7q21), D10S677 (10q23), D15S128 (15Q11), D16S3401 (16p), and D17S2193 (17q24) in breast tumor stroma of the individual, or a combination thereof, wherein the presence of a mutation of the TP53 gene, LOH/AI at the one or more loci, or a combination thereof in the breast tumor stroma indicates nodal metastasis of the breast tumor in the individual.

As used herein, "breast cancer" refers to a variety of breast cancers such as hereditary breast cancer or sporadic breast cancer. In one aspect, the breast cancer is a sporadic breast cancer. In another aspect, the breast cancer is an invasive ductal carcinoma.

Heterozygosity denotes the presence of two alleles which can be individually discriminated by slight, minor differences in DNA sequence commonly found at microsatellites, which are segments of DNA composed of variable numbers of short repeat units that occur in predictable locations within the genome but vary in absolute length according to the number of repeats. Microsatellite markers can be used to evaluate the two different copies or alleles of the human genome. In the normal state, the two alleles can be distinguished from a each other and are said to exist in a state of heterozygosity. When mutations are acquired which typically involve deletion of all or part of an allele, one of the two copies is lost from the cell by deletion leading to a loss of heterozygosity.

"Loss of heterozygosity/allelic imbalance" typically refers to the loss of a portion of a chromosome in somatic cells (e.g., a deletion, mutation, or loss of an entire chromosome (or a region of the chromosome) from the cell nucleus). Since only one of the two copies of the affected chromosomal region originally present in an individual's genome will remain in cells which have undergone LOH, all polymorphic markers within the region will appear to be homozygous; i.e., these cells will have lost heterozygosity for these markers. Comparison of marker genotypes in a population of cells that are suspected of having undergone LOH with genotypes of normal tissue from the same individual allows for the identification of LOH, and for mapping the extent of the loss.

In particular embodiments, the LOH/AI is at one or more of the following loci: D7S821 (7q21), D10S677 (10q23), D15S128 (15q11), D16S3401 (16p), D17S2193 (17q24)).

The methods described herein encompass detecting a variety of mutations in the TP53 gene (e.g., of the epithelium, stroma and or combination thereof). See, for example, Table 7.

In the methods of the invention, a sample can be obtained from the individual and used in the methods to detect the presence of the LOH/AI and/or mutation in the TP53 gene. The LOH/AI and/or mutation in the TP53 gene can be detected in any sample obtained from the individual that comprises the individual's DNA. For example, a LOH/AI and/or mutation in the TP53 gene can be detected in a tissue sample (e.g., skin, muscle, organ, placenta), a cell sample (e.g., fetal cells), a fluid sample (e.g., blood, amniotic fluid, cerebrospinal fluid, urine, lymph) and any combination thereof. Such samples can be obtained from the breast cancer (e.g., the breast tumor) and/or the microenvironment of the breast cancer (e.g., the stroma (e.g., stromal cells) and/or epithelium (e.g., neoplastic epithelial cells) surrounding the breast tumor). Methods of obtaining such samples a or extracting nucleic acid from such samples are described herein and known to those of skill in the art.

Methods of obtaining such samples are well known in the art. In a particular embodiment, the presence of a LOH/AI at one or more specific loci and/or mutation in the TP53 gene can be detected in a sample (e.g., tissue, cell, fluid) from the tumor epithelium and/or the surrounding stroma of the tumor epithelium in the individual. The tumor epithelium and/or surrounding stroma can be obtained using any suitable method known in the art such as laser capture microdissection (LCM). In addition, the DNA can be extracted and amplified, and the LOH/AI at one or more specific loci and/or mutation in the TP53 gene can be detected, using any suitable methods known in the art, as described herein. As will be apparent to one of skill in the art, methods other than those described herein can be used.

In particular embodiments, the presence of LOH/AI at one or more of the loci and/or mutation in the TP53 gene are detected in stromal cells (e.g., non-malignant stromal cells, malignant stromal cells) surrounding the tumor. The stromal cells can be, for example, fibroblast cells present in the stroma. In another embodiment, the presence of LOH/AI at one or more of the loci and/or mutation in the TP53 gene are detected in epithelial cells of the tumor (epithelial tumor cells).

A variety of methods can be used to detect the presence of LOH/AI at one or more of the loci and/or mutation in the TP53 gene of an individual. Examples of such methods include laser-capture microdissection to procure neoplastic tissue (e.g., stroma, epithelium), polymerase chain reaction (PCR), gel electrophoresis, and/or immunohistochemical analysis.

The presence of the LOH/AI and or a mutation of the TP53 gene described herein can be detected in any sample obtained from the individual that comprises the individual's nucleic acid (e.g., genomic DNA). Methods of obtaining such samples are well known in the art. In a particular embodiment, the presence of a LOH/AI at one or more specific loci can be detected in a sample (e.g., tissue, cell, fluid) from the tumor epithelium and/or the surrounding stroma (e.g., breast tumor stroma) of the tumor epithelium in the individual. As used herein a cell can be a germ cell or somatic cell. Suitable cells can be of, for example, mammalian (e.g., human) origin. The tumor epithelium and/or surrounding stroma can be obtained using any suitable method known in the art such as laser capture microdissection (LCM). In addition, the genomic DNA can be extracted and amplified, and the LOH/AI at one or more specific loci in the genome of the individual can be detected, using any suitable methods known in the art, as described herein. As will be apparent to one of skill in the art, methods other than those described herein can be used.

The detection of the LOH/AI and/or mutation in the TP53 gene in the individual can be compared to a control. Suitable controls for use in the methods provided herein are apparent to those of skill in the art. For example, a suitable control can be established by assaying one or more (e.g., a large sample of) individuals which do not have the LOH/AI at the loci described herein. Alternatively, a control can be obtained using a statistical model to obtain a control value (standard value; known standard). See, for example, models described in Knapp, R. G. and Miller M. C. (1992) Clinical Epidemiology and Biostatistics, William and Wilkins, Harual Publishing Co. Malvern, Pa., which is incorporated herein by reference.

The LOH/AI at the one or more specific loci and/or mutation in the TP53 gene in individuals with breast cancer described herein can also be used as targets for therapeutic and/or preventive intervention of breast cancer in an individual. Identification of the markers of the breast cancer described herein provide for methods of detecting recurrence of the cancer in an individual that is in remission, or has been treated for the cancer comprising detecting the markers in the individual.

In addition, the markers provide for methods of screening an asymptomatic individual for breast cancer comprising detecting the marker in the asymptomatic individual.

Also encompassed by the present invention are methods of monitoring a treatment regimen for breast cancer in an individual comprising monitoring the marker(s) in an individual undergoing a particular treatment regimen. Alternatively, the present invention provides methods of monitoring an individual that has previously received treatment for breast cancer comprising monitoring the marker(s) in the individual.

As used herein the term "individual" includes animals such as mammals, as well as other animals, vertebrate and invertebrate (e.g., birds, fish, reptiles, insects (e.g., *Drosophila* species), mollusks (e.g., *Aplysia*). Preferably, the animal is a mammal. The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include primates (e.g., humans, monkeys, chimpanzees), canines, felines, rodents (e.g., rats, mice, guinea pigs) and ruminents (e.g., cows, pigs, horses).

Also provided herein are kits for use in diagnosing breast cancer or susceptibility to breast cancer, and/or detecting nodal metastasis of a breast cancer (e.g., a breast tumor) in an individual comprising one or more regents for detecting the presence of a LOH/AI at one or more loci selected from the group consisting of: D7S821 (7q21), D10S677 (10q23), D15S128 (15q11), D16S3401 (16p), D17S2193 (17q24)) and/or mutation in the TP53 gene. For example, the kit can comprise primers for us in a polymerase chain reaction (PCR) (e.g., see Table 5), hybridization probes, restriction enzymes (e.g., for RFLP analysis), allele-specific oligonucleotides, and antibodies. In a particular embodiment, the kit comprises at least one contiguous nucleotide sequence that is substantially or completely complementary to a region of one or more of the loci comprising the LOH/AI. For example, the nucleic acids can comprise at least one sequence (contiguous sequence) which is complementary (completely, partially) to one or more loci comprising LOH/AI that is associated with breast cancer. In one embodiment, the one or more reagents in the kit are labeled, and thus, the kits can further comprise agents capable of detecting the label. The kit can further comprise instructions for using the components of the kit.

Experimentation

Methods
Patients

Invasive breast cancer from 218 patients (43 with hereditary breast cancer and 175 with sporadic breast cancer) was evaluated. For both groups, inclusion criteria were a pathologic diagnosis of invasive ductal carcinoma and a clinical stage with no known metastases. Patients with widely metastatic disease were excluded to minimize incomplete ascertainment due to the difficulty of obtaining the original primary carcinoma, on which all analyses were performed.

Patients with hereditary breast cancer had to meet clinical diagnostic criteria (Genetic/familial high-risk assessment: breast and ovarian cancer. Jenkintown, Pa.: National Comprehensive Cancer Network (NCCN), 2007 www.nccn.org/professional/physician_gls/PDF/genetics_screening.pdf.) and have deleterious germ-line mutations or unclassified variants of BRCA1 or BRCA2. Two patients whose tumors were wild-type for both genes were included in the hereditary group because they were members of families with a high previous probability of harboring BRCA1 or BRCA2 mutations.

The institutional review board at each participating institution approved the study (under exempt status). Anonymous samples linked only to clinicopathological data obtained from September 2005 to May 2007 were used.

Laser Capture Microdissection and DNA Extraction

Laser-capture microdissection was performed with the use of an Arcturus PixCell II microscope (Arcturus Engineering) to procure epithelium and stroma of the neoplastic tissue (Fukino K, et al., *Cancer Res* 2004:64:7231-6; Kurose K. et al., *Hum Mol Genet* 2001:10:1907-13). This microscope uses a transparent thermoplastic film (also called a standard laser-capture microdissection cap) applied to the surface of the tissue section (5 to 7 µm thick) on standard histopathology slides. The epithelial cells, surrounding stromal cells, and normal cells in the sample were identified and targeted through a microscope, with a relatively narrow (15 to 30 µm) carbon dioxide laser-beam pulse. The resulting strong focal adhesion allowed selective procurement of only the target cells.

First, the neoplastic epithelium was removed and the fibroblasts in the stroma were then taken. Four to six standard laser-capture microdissection caps (with 8000 to 9000 cells per cap) were procured per compartment (four from the epithelial compartment and six from the stromal compartment which is less cellular/unit area). Stromal fibroblasts residing between aggregations of epithelial tumor cells or no more than 0.5 cm distant from the tumor nodule were specifically captured. This morphological approach allows for replication of the distances between the tumor-stromal and tumor-epithelial fractions for all samples.

DNA for each tumor was also obtained from peripheral-blood leukocytes (in 75% of hereditary tumors) or normal-appearing cells that were at least 1 cm distant from the tumor in the tissue section. The origin of the normal DNA had no effect on the frequency or pattern of loss of heterozygosity or allelic imbalance. After the performance of laser-capture microdissection, genomic DNA was extracted as described (Fukino K, et al., *Cancer Res* 2004:64:7231-6; Kurose K. et al., *Hum Mol Genet* 2001:10:1907-13; Marsh D J, et al., *Cancer Res* 1997:57:500-3).

Genomewide Scan

Polymerase chain reaction (PCR) was performed on DNA from each compartment (normal, epithelium, and stroma) of each sample and one of 72 multiplex primer panels, comprising 372 and 386 fluorescent-labeled microsatellite markers for hereditary and sporadic samples, respectively. These markers are distributed throughout chromosomes 1 to 22 and X and are based on the MapPairs Human Markers set, version 10 (Invitrogen) development at the Marshfield Institute. This genomewide panel has an average of 16.2 markers per chromosome (ranging from 7 to 29 markers per chromosome) or an intermarker distance of approximately 9 cM.

Genotyping was performed with either the ABI 3700 or the 3730 XL semiautomated sequencer (Applied Biosystems). The results were analyzed by automated fluorescence detection with the use of the GeneScan collection and analysis software (Applied Biosystems). Scoring for the loss of heterozygosity to allelic imbalance was performed by visual inspection of the GeneScan output. A ratio of allele peak heights between germ-line DNA and somatic DNA of 1.5 or more was used to define a loss of heterozygosity or allelic imbalance (Nelson H H, et al., *Carcinogenesis* 2005; 26:1770-3; Dacie S., et al., *Am J Surg Pathol* 2005:29:897-902). The reliability of such evaluations by multiplex PCR on archived tissue has been extensively validated (Fukino K, et al., *Cancer Res* 2004:64:7231-6).

Mutation Analysis of TP53

Mutation analysis of TP53 was performed by PCR amplification of exons 4 to 9 of TP53, followed by denaturing gradient gel electrophoresis (DGGE) analysis. Fragments showing abnormal migration patterns in the DGGE analysis were reamplified from the original DNA and directly sequenced. A description of the PCR conditions and oligonucleotide primer sequences used for PCR-DGGE and sequencing is available in Table 4. DGGE separation through a 10% polyacrylamide gel containing a 20 to 70% urea-formamide gradient was performed at 120 V and 60° C. for 14 hours (Rines R D, et al., *Carcinogenesis* 1998:19:979-84).

Immunohistochemical Analysis

Paraffin sections of breast-cancer specimens were rehydrated and subjected to microwave antigen retrieval for 20 minutes followed by overnight incubation 4'C with antibodies against p53 from murine clone PAb1801 (Novocastra) at a dilution of 1:300. Slides were washed and incubated with secondary biotinylated antibodies with the use of the Vectastain ABC kit (Vector Laboratories); they were then treated with sequential additions of avidin peroxidase and 3,3'-diaminobenzidine and counterstained by methyl green. The status of p53 was scored visually as positive by a generalized linear-regression model if the nuclei of stromal calls stained darkly.

Statistical Analysis

A total of 372 microsatellite markers from the 43 hereditary cancers and 386 markers from the 175 sporadic breast cancers were analyzed in the samples obtained from the epithelium and stroma. Chi-square tests of association between the loss of heterozygosity and TP53 mutation in these two groups of tumors were performed. The Wilcoxon rank-sum test was applied to compare frequencies of the loss of heterozygosity between each paired group with wild-type TP53 with the mutated TP53.

To identify compartmental hot spots of the loss of heterozygosity associated with mutated TP53, the significance of overall frequencies (across all samples), as compared with chromosome-average frequencies, of the loss of heterozygosity was analyzed for each microsatellite marker with the use of logistic regression with TP53 as a covariate; the significance of the presence of a TP53 mutation was additionally tested with the use of analysis of deviance. These statistical methods are meant to identify microsatellite loci with the highest degree of association between a loss of heterozygosity or allelic imbalance and TP53 mutation. Logistic regression and analysis of deviance were also applied to test the association between loss of heterozygosity or allelic imbalance and each of the clinical and pathological features (pathologically confirmed tumor and nodal status, tumor grade, clinical stage, estrogen-receptor status, and expression of HER2/neu). For this analysis, the age at diagnosis was taken into account by including it as a covariate. Adjustment for multiple testing was applied with the use of false positive report probability (FPRP) (Wacholder S. et al., *J Natl Cancer Inst* 2004:96:434-42; Weber F., et al., *JAMA* 2007:297:187-95). A significant FPRP value with a previous probability of 0.01 and an FPRP value of less than 50% is denoted as $FPRP_{0.01} < 0.5$.

Among the microsatellite markers that had a significant association with mutated TP53 in the stroma of the sporadic cancers, linear-by-linear association tests (Agtesti A. Categorical data analysis. Hoboken, N.J. Wiley-interscience, 2002; Hothorn L A. *J Biopharm Stat* 2006:16:711-31) were used to identify markers having a significant association with lymph-node metastases. This test seeks associations between lymph-node status and each stromal microsatellite marker, stratified according to TP53 mutation status. If a significant association was found, then which TP53 status (mutation-positive or mutation-negative) was associated with nodal involvement was determined. Multiple-testing adjustments were controlled by a false discovery rate of less than 0.1.

The R package (http://www.r-project.org) was used for all data mining and statistical analysis.

Results

Patients

Table 5 summarizes the clinical and pathological features of all patients. The mean age at diagnosis was 42.6 years (range, 23 to 86) in the group with hereditary cancers (hereditary group) and 52.3 years (range, 25 to 82) in the group with sporadic cancers (sporadic group) (P=0.002). Positivity for either the estrogen receptor or the progesterone receptor was less frequent in the hereditary group than in the sporadic group (64% vs. 41%, P=0.02). There were no significant differences in tumor stage and nodal status between the two groups. The patients' demographic and clinical characteristics and pathological features of the tumor samples are consistent with those of results reported previously (Honrado E. et al., *Mod Pathol* 2005:18:1305-20).

TP53 Mutations

Figure 1B:
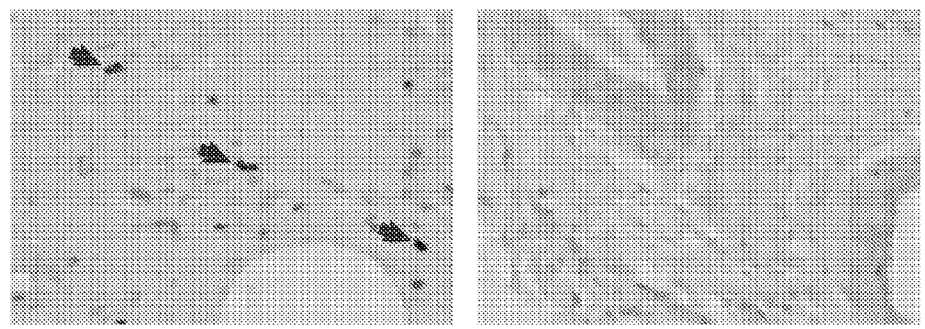
Figure 1C:
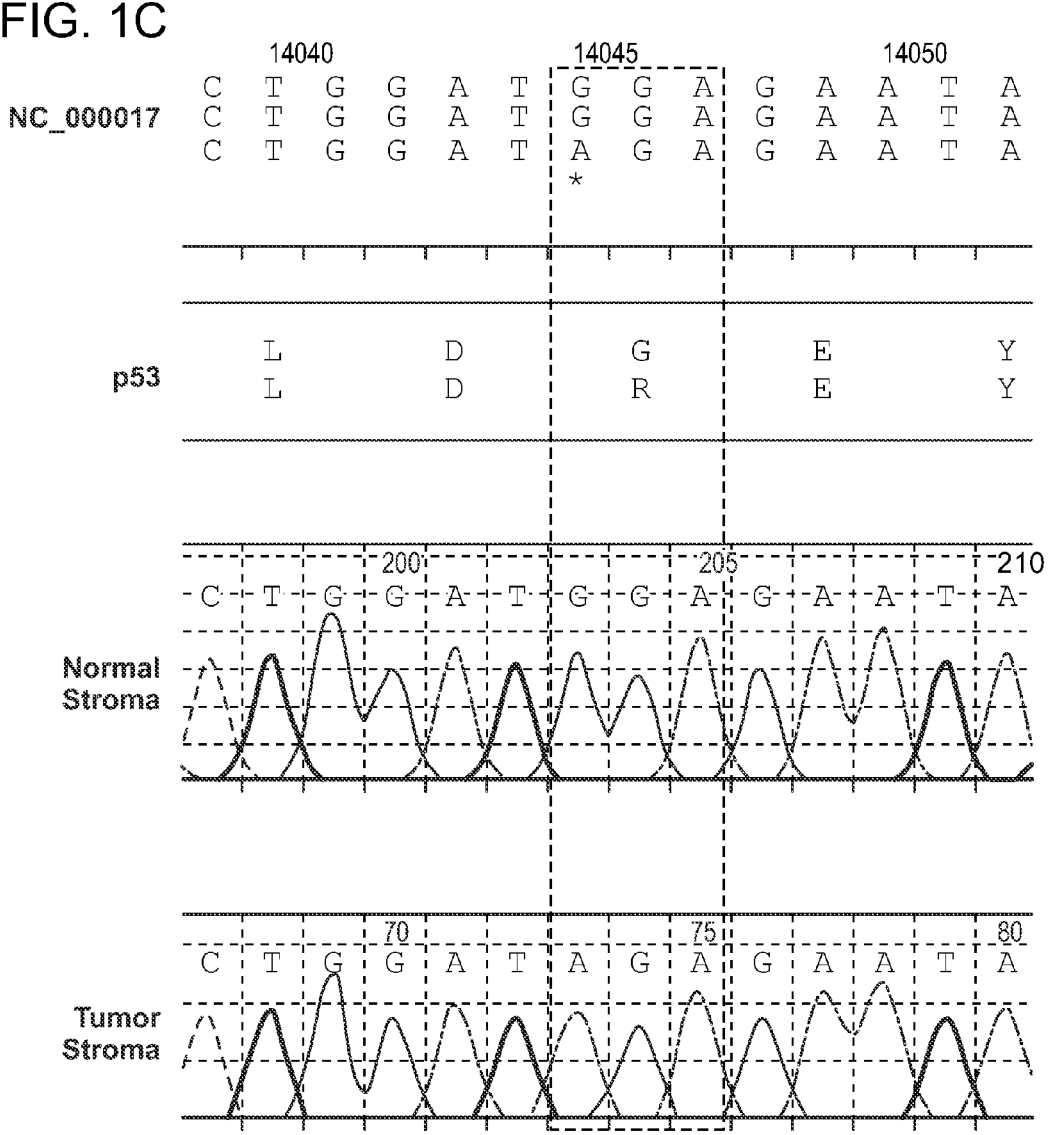

A total of 32 of 43 samples from the hereditary group (74.4%) and 74 of 175 samples in the sporadic group (42.3%) had TP53 mutations (P<0.002) (FIGS. 1A-1C, and Tables 6 and 7). Of the samples with TP53 mutations in the hereditary group, 11 (25.6%) had mutations in epithelium alone, 11 (25.6%) had mutations in stroma alone, and 10 (23.3%) had mutations in both compartments. Of the samples with TP53 mutations in the sporadic group, 26 (14.9%) had mutations in epithelium alone, 34 (19.4%) had mutations in stroma alone, and 14 (8.0%) had mutations in both compartments, similar to our preliminary data (Agtesti A. Categorical data analysis. Hoboken, N.J. Wiley-interscience, 2002) (FIG. 1A). Of 45 breast cancers with sequence-confirmed TP53 missense mutations, 2 samples showed nuclear staining for p53 in tumor stroma but not normal stroma (FIG. 1B).

Loss of Heterozygosity or Allelic Imbalance

The frequencies of loss of heterozygosity or allelic imbalance in epithelium and stroma in the hereditary group were higher than in the sporadic group. The median frequency of loss of heterozygosity or allelic imbalance in the neoplastic epithelium was 67% in the hereditary group and 54% in the sporadic group (P<0.001). The median frequency of the loss of heterozygosity or allelic imbalance in stroma was 60% in the hereditary group and 51% in the sporadic group (P<0.001) (Table 1). It was found that a TP53 mutation in epithelium or stroma was associated with an increased frequency in loss of heterozygosity or allelic imbalance in both the hereditary group and the sporadic group, but the association was more pronounced in the sporadic group (Table 2). There was no significant difference in overall loss of heterozygosity or allelic imbalance in breast cancers from patients with deleterious BRCA1 or BRCA2 mutations or those with unclassified variants, uvBRCA1 or uvBRCA2 (data not shown).

Figure 2:
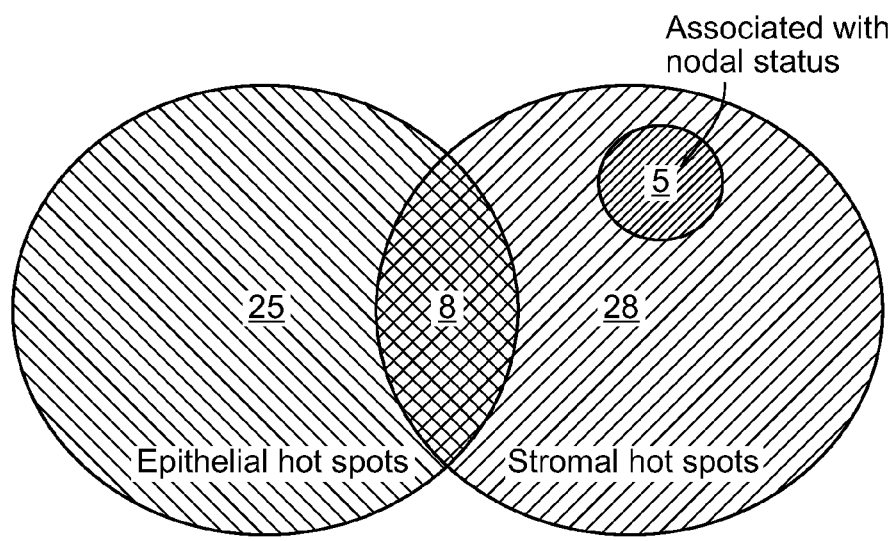
FIG. 2 shows 66 hot spots of Loss of Heterozygosity or Allelic Imbalance Associated with Stromal TP53 Mutations in Sporadic Breast Cancer. In this Venn diagram, of the 66 (25+8−28+5) hot-spot markers, only 8 markers of loss of heterozygosity or allelic imbalance that are common to both epithelium and stroma are associated with stromal TP53 mutations, as compared with 25 in the epithelium alone and 33 (28+5) in the stroma alone. Among the hot-spot markers, only a loss of heterozygosity of allelic imbalance at the five stromal markers is associated with increased regional nodal metastases in the setting of wild-type p53.

Whether compartment-specific TP53 mutations are associated with loss of heterozygosity or allelic imbalance at specific microsatellite markers was then tested. Markers with a significantly higher frequency of loss of heterozygosity or allelic imbalance than all other markers on the same chromosome are considered to be hot spots (Fukino K, et al. *Cancer Res* 2004:64:7231-6; Weber F. et al., *Am J Hum Genet* 2006: 78:961-72). Among all samples in the sporadic group, 66 hot-spot loci linked to a loss of heterozygosity or allelic imbalance that were associated with a compartmental TP53 mutation were identified (at P<0.05 and $FPRP_{0.01} < 0.5$) (FIG. 2). Thus, these 66 loci harbored a loss of heterozygosity or allelic imbalance at frequencies significantly higher than could be obtained by chance. This association holds across all tumors and compartments but cannot be ascertained for a single tumor. Of these 66 hot-spot markers, 8 markers— D2S2944 (2q34), D3S1262 (3q27), D5S1462 (5q15), D7S1818 (7p12), D15S128 (15q11), D16S2616 (16p13), D18S1390 (18q23), and D20S103 (20p13)—occurred in both epithelium and stroma, and each was associated with the presence of a TP53 mutation (FIG. 2, and Table 8). Of the remaining 58 hot spots, 25 were found only in epithelium and 33 were detected only in stroma (FIG. 2, Tables 9, 10, and 11). It was also found that stromal TP53 mutations were associated with loss of heterozygosity or allelic imbalance at 41 stromal hot-spot markers (FIG. 2). In the hereditary group, there was only one hot spot of loss of heterozygosity or allelic imbalance associated with a TP53 mutation, specifically at D2S1400 (2p25.1) in the stroma (at P<0.05 and $FPRP_{0.01} < 0.5$) (Table 9).

Association with Clinical and Pathological Features

Figure 3:
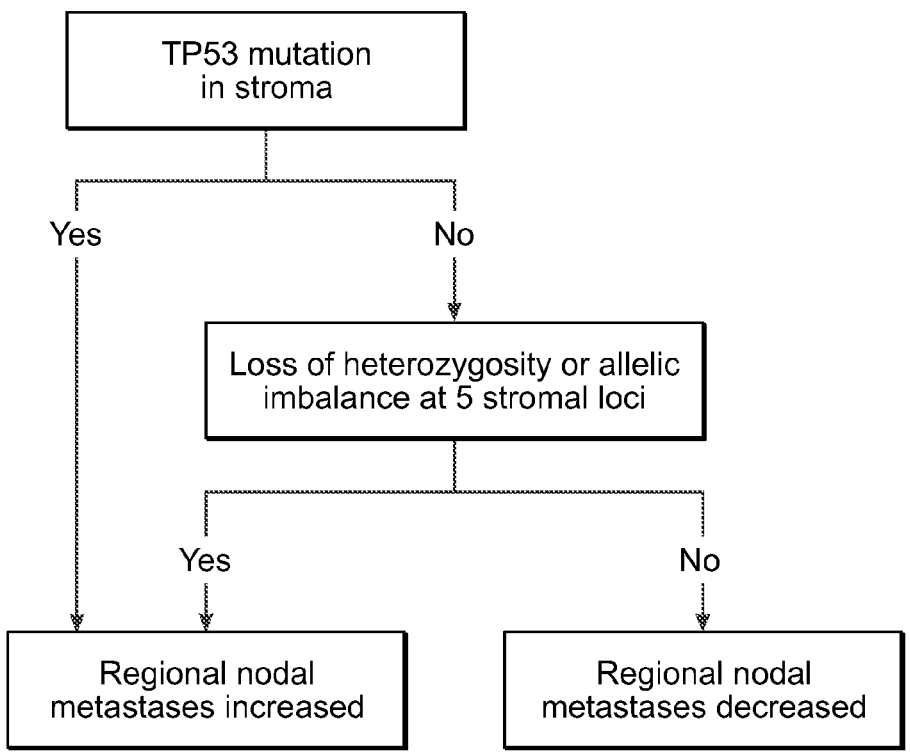
FIG. 3 shows somatic TP53 Mutation or Loss of Heterozygosity or Allelic Imbalance at Five Stromal Markers Associated with increased Locoregional Lymph-Node Metastases in Sporadic Breast Cancer.

A significant association between the TP53 mutation status in stroma and lymph-node status (P=0.003) was found only in the sporadic group (Table 12). Moreover, TP53 mutations in stroma were associated with nodal metastases only in the sporadic group (FIG. 3). Loss of heterozygosity or allelic imbalance at five stromal hot-spot markers—D7S821 (7q21), D10S677 (10q23), D15S128 (15Q11), D16S3401 (16p), and D17S2193 (17q24)—that were associated with nodal metastases in the absence of TP53 mutations in the tumor stroma were also identified (at P<0.05 and FDR<0.1) (Table 3 and FIG. 3). Thus, stromal TP53 mutation alone and stromal loss of heterozygosity at five hot-spot loci alone were both associated with nodal metastases. There was no additive effect of the presence of TP53 mutation and loss of heterozygosity or allelic imbalance at these five loci (P>0.05) (Table 2 and FIG. 3).

Discussion

The results of the few studies that have investigated the prognostic value of TP53 mutations in breast and other cancers are contradictory (Overgaard J. et al., *Acta Oncol* 2000: 39:327-33; Bissa S. et al., *Anticancer Res* 1997:17:3091-7; Pharoah P D, et al., *Br J. Cancer* 1999:80:1968-73). Described herein is the evaluation of the associations between the presence of TP53 in the tumor, genomic alterations in the tumor microenvironment and presenting clinical and pathological findings in two groups of tumors: hereditary breast cancers associated with BRCA1 or BRCA2 mutations and sporadic breast cancers.

In studies of epithelium and stroma from hereditary breast cancers with germ-line BRCA1 or BRCA2 mutations, frequencies of loss of heterozygosity or allelic imbalance were higher than those in sporadic breast cancers (Weber F. et al., *Am J Hum Genet* 2006:78:961-72). The TP53 mutations in familial breast cancers often retain their activities that induce apoptosis, up-regulate genes, and inhibit growth (Fukino K, et al., *Cancer Res* 2004:64:7231-6), in most cases, however, the TP53 mutations in hereditary and sporadic breast cancers differ in their position along the gene. It was found that TP53 mutations in the stroma of hereditary and sporadic breast cancers were associated with an increased frequency of loss of heterozygosity or allelic imbalance across all microsatellite markers. Despite this overall increase, only one marker in the 43 hereditary breast cancers was found that was identified as a hot spot associated with mutant TP53: marker D2S1400 on 2p25.1, containing E2F6, a transcription factor that targets BRCA1 and has an important role in the regulation of apoptosis (Yang W W, et al., *Cell Death Differ* 2007:14:807-17).

Unlike hereditary breast cancer, sporadic breast cancer does not have an underlying generalized genomic instability (Weber F. et al., *Am J Hum Genet* 2006:78:961-72). Nevertheless, it was found that TP53 mutations in sporadic breast cancer were associated with 66 hot-spot markers of loss of heterozygosity or allelic imbalance. The eight hot spots associated with TP53 mutations in both epithelium and stroma map to regions that encode proteins in p53-related pathways. For example, 3q27.3 (D3S1262) contains TP73L, a member of the TP53 gene family; p63, encoded by TP73L, is expressed exclusively in the myoepithelial cells of normal breast tissue, and its decreased expression in breast cancer is associated with disease progression (Wang X, et al., *Breast Cancer* 2002:9:216-9). In addition, certain markers identified as hot spots only in TP53-mutated epithelium map to chromosomal regions containing genes that encode p53 targets. Thus, sporadic breast cancers must have multiple mechanisms that disrupt normal cellular regulation, such as cell-cycle progression and checkpoints, DNA repair, and apoptosis. The data provided herein indicate that these mechanisms, whether in play in stroma or epithelium, involve p53.

The overall frequency of loss of heterozygosity or allelic imbalance was similar in the epithelial and stromal compartments of sporadic breast cancers. Somatic TP53 mutations in the stroma were associated with loss of heterozygosity or allelic imbalance of chromosomal regions harboring p53-related genes. The significant association between stromal TP53 mutations and nodal metastases in sporadic breast cancers suggests that such mutation-bearing stromal cells provide a favorable microenvironment for tumor spread (FIG. 3). It was also found that even in the absence of TP53 mutations in stroma of sporadic breast cancers, loss of heterozygosity or allelic imbalance at five microsatellite markers was associated with nodal metastases. The D10D677 marker (10q23.3) maps to a region containing the gene that encodes phospholipase C, epsilon 1 (PLCE1); this enzyme catalyzes the hydrolysis of polyphosphoinositides and thereby initiates in the growth and differentiation of cells PLC-ε, the corresponding protein, mediates the effects of the small guanosine triphosphatases belonging to the Ras superfamily on the actin cytoskeleton and membrane protrusion (Ada-Nguema A S, et al., *J Cell Sci* 2006:119:2301-19). Another marker, D16S3401 (16p13.3), maps to a region containing the gene encoding nonmetastatic cells 4 (NME4), a member of the nucleoside diphosphate kinase family. The function of NME4 protein is unknown, but another NME family member, NME1, is regulated by p53 and decreases metastatic potential (Chen S L, et al., *Mol Carcinog* 2003:36:204-14).

The observations described herein indicate that TP53-mutated stroma or loss of heterozygosity or allelic imbalance at five specific stromal markers accelerates tumor progression. Corroboration of the results in a larger prospective study would be useful, however, the results herein show that analysis of breast-tumor stroma for the presence of TP53 mutations and loss of heterozygosity or allelic imbalance at the five markers are likely helpful to predict nodal status (FIG. 3). Although the procurement of stroma by laser-capture microdissection is currently complex and perhaps beyond routine clinical use, analysis of TP53 mutation and of the five microsatellite markers for loss of heterozygosity or allelic imbalance involves techniques that are routinely used in clinical laboratories (Patocs, A., et al., *NEJM*, 357(25):2543-2551 (2007, which is incorporated by reference herein in its entirely).

TABLE 1

Frequency of Loss of Heterozygosity or Allelic Imbalance in 175 Sporadic Breast Cancers and 43 Hereditary Breast Cancers in Epithelium and Stroma.*

| Tissue | Sporadic Group | | Hereditary Group | | |
| --- | --- | --- | --- | --- | --- |
| | No. of Markers | LOH Frequency | No. of Markers | LOH Frequency | P Value† |
| Epithelium | 370 | | 367 | | <0.001 |
| Median | | 0.54 | | 0.67 | |
| Interquartile range | | 0.45-0.64 | | 0.57-0.78 | |
| Stroma | 370 | | 368 | | <0.001 |
| Median | | 0.51 | | 0.60 | |
| Interquartile range | | 0.41-0.62 | | 0.50-0.71 | |

*LOH denotes loss of heterozygosity or allelic imbalance.

†P values were calculated with the Wilcoxon rank-sum test.

TABLE 2

Frequency of Loss of Heterozygosity or Allelic Imbalance in Stroma and Epithelium of Hereditary and Sporadic Breast Cancers, According to the Type of TP53 Mutation.*

| Tissue | Mutated TP53 No. of Markers | Mutated TP53 LOH Frequency | Wild-Type TP53 No. of Markers | Wild-Type TP53 LOH Frequency | P Value† |
|---|---|---|---|---|---|
| Hereditary group | | | | | |
| Epithelium | 370 | | 367 | | 0.01 |
| Median | | 0.61 | | 0.67 | |
| Interquartile range | | 0.50-0.71 | | 0.50-0.80 | |
| Stroma | 370 | | 368 | | <0.001 |
| Median | | 0.70 | | 0.57 | |
| Interquartile range | | 0.60-0.78 | | 0.40-0.71 | |
| Sporadic group | | | | | |
| Epithelium | 384 | | 385 | | <0.001 |
| Median | | 0.62 | | 0.47 | |
| Interquartile range | | 0.54-0.69 | | 0.40-0.54 | |
| Stroma | 384 | | 385 | | <0.001 |
| Median | | 0.60 | | 0.42 | |
| Interquartile range | | 0.53-0.66 | | 0.36-0.50 | |

*LOH denotes loss of heterozygosity or allelic imbalance.
†P values were calculated with the Wilcoxon rank-sum test.

TABLE 3

Associations among Hot Spots of Loss of Heterozygosity or Allelic Imbalance in Stroma, TP53 Mutation Status, and Nodal Status in Sporadic Breast Cancer.*

| Marker | Locus | LOH Frequency in Wild-Type TP53 Nodal Status 0 | 1 | 2 or 3 | P Value† | LOH Frequency in Mutated TP53 Nodal Status 0 | 1 | 2 or 3 | P Value† |
|---|---|---|---|---|---|---|---|---|---|
| D7S821 | 7q21.3 | 0.39 | 0.41 | 0.88 | 0.04 | 0.60 | 1 | 1 | 0.06 |
| D10S677 | 10q23.3 | 0.24 | 0.48 | 0.83 | 0.004 | 0.64 | 0.60 | 0.75 | 0.77 |
| D15S128 | 15q11.2 | 0.19 | 0.41 | 0.67 | 0.02 | 0.50 | 0.25 | 1 | 0.12 |
| D16S3401 | 16p13.3 | 0.22 | 0.36 | 0.83 | 0.007 | 0.63 | 0.40 | 1 | 0.18 |
| D17S2193 | 17q24.2 | 0.32 | 0.48 | 0.88 | 0.01 | 0.63 | 0.50 | 0.83 | 0.46 |

*LOH denotes loss of heterozygosity or allelic imbalance.
†P values are for the overall comparisons among the nodal-status subgroups. Multiple-testing adjustments were controlled so that a false positive finding would occur less than 10% of the time.

TABLE 4

Clinicopathological Features of Breast Cancer Patients

| | Sporadic | Hereditary breast cancer | p-value |
|---|---|---|---|
| Number of cases | n = 174 | n = 43 | |
| Age (years) (range) | 52.3 (25-82) | 42.6 (23-86) | P = 0.002* |
| Tumor stage (%, n/d) | | | |
| 0-I | 29.8 (42/141) | 20.5 (7/34) | P = 0.55 |
| II | 50.3 (71/141) | 58.8 (20/34) | |
| III | 19.8 (28/141) | 20.5 (7/34) | |
| Non-informative | 34/175 | 9/43 | |
| Nodal status (%, n/d) | | | |
| 0 | 47.6 (60/126) | 52.9 (18/34) | P = 0.58 |
| >1 | 52.4 (66/126) | 47.1 (16/34) | |
| Non-informative | 49/175 | 9/43 | |
| Estrogen receptor status (%, n/d) | | | |
| Positive | 64.9 (100/154) | 41.3 (12/29) | P = 0.017* |
| Negative | 35.0 (54/154) | 58.6 (17/29) | |
| Non-informative | 21/175 | 14/43 | |

TABLE 4-continued

Clinicopathological Features of Breast Cancer Patients

|  | Sporadic | Hereditary breast cancer | p-value |
|---|---|---|---|
| Progesterone receptor status (%, n/d) | | | |
| Positive | 64.9 (100/154) | 41.3 (12/29) | P = 0.017* |
| Negative | 35.0 (54/154) | 58.6 (17/29) | |
| Non-informative | 21/175 | 14/43 | |

*indicates a significance with P value < 0.05.
A binomial model with nested structure was used to compare the distributions of clinicopathological features for patients with germline BRCA 1/2 mutations/variants to sporadic breast cancer patients.
(%, n/d) denotes percentage (numerator divided by denominator)

TABLE 5

Primers Used For DGGE and Sequencing of TP53

| | 5' - 3' | TM (° C.) |
|---|---|---|
| Sequencing Primers | | |
| P53-4Fseq | CCTGGTCCTCTGACTGCTCTTTTCACCCA (SEQ ID NO: 1) | 55 |
| P53-4Rseq | GGCCAGGCATTGAAGTCTCAT (SEQ ID NO: 2) | |
| P53-5Fseq | CAACTCTGTCTCCTTCCT (SEQ ID NO: 3) | 55 |
| P53-5Rseq | TGTCGTCTCTCCAGCCCC (SEQ ID NO: 4) | |
| P53-6Fseq | AGAGACGACAGGGCTGGTTG (SEQ ID NO: 5) | 55 |
| P53-6Rseq | CTTAACCCCTCCTCCCAGAG (SEQ ID NO: 6) | |
| P53-7Fseq | CCTCATCTTGGGCCTGTGTT (SEQ ID NO: 7) | 55 |
| P53-7Rseq | AGTGTGCAGGGTGGCAAGTG (SEQ ID NO: 8) | |
| P53-8Fseq | CCTTACTGCCTCTTGCTTCT (SEQ ID NO: 9) | 55 |
| P53-8Rseq | ATAACTGCACCCTTGGTCTC (SEQ ID NO: 10) | |
| P53-9Fseq | GGAGACCAAGGGTGCAGTTATGCCTCAG (SEQ ID NO: 11) | 55 |
| P53-9Rseq | CCCAATTGCAGGTAAAACAG (SEQ ID NO: 12) | |
| DGGE PRIMERS | | |
| P53-4.1F | CGTCCCGCTGGTCCTCTGACTGCTCTTT (SEQ ID NO: 13) | 55 |
| P53-4.1R | CGCCCGCCGCGCCCCGCGCCCGTCCCGCCGCCCCC GCCCGCATTCTGGGAGCTTCATCTG (SEQ ID NO: 14) | |
| P53-4.2F | AAGCTCCCAGAATGCCAG (SEQ ID NO: 15) | 55 |
| P53-4.2R | CGCCCGCCGCCGCCCGCCGCGCCCCGCGCCCGTCC CGCCGCCCCCGCCCGGCAAGAAGCCCAGACGGA (SEQ ID NO: 16) | |
| P53-4.3F | CGCCCGCCGCCGCCCGCCGCGCCCCGCGCCCGTCC CGCCGCCCCCGCCCGTCCCTTCCCAGAAAACCT (SEQ ID NO: 17) | 55 |
| P53-4.3R | TGAAGTCTCATGGAAGCC (SEQ ID NO: 18) | |
| P53-5F | CGCCCGCCGCCGCCCGCCGCGCCCCGCGCCCGTCC CGCCGCCCCCGCCCGCAACTCTGTCTCCTTCCT (SEQ ID NO: 19) | 62 |
| P53-5R | TGTCGTCTCTCCAGCCCC (SEQ ID NO: 20) | |

TABLE 5-continued

Primers Used For DGGE and Sequencing of TP53

| | 5' - 3' | TM (° C.) |
|---|---|---|
| P53-6F | AGAGACGACAGGGCTGGTTG (SEQ ID NO: 21) | 62 |
| P53-6R | CGCCCGCCGCGCCCCGCGCCCGGCCCGCCGCCCC CGCCCGAAATAATAAACCTTAACCCCTCCTCCC AGA (SEQ ID NO: 22) | |
| P53-7F | CGCCCGCCGCGCCCCGCGCCCGTCCCGCCGCCCC CGCCCG-CCTCATCTTGGGCCTGTGTT (SEQ ID NO: 23) | 57 |
| P53-7R | AGTGTGCAGGGTGGCAAGTG (SEQ ID NO: 24) | |
| P53-8F | CGCCCGCCGCGCCCCGCGCCCGTCCCGCCGCCCC GCCCG-CCTTACTGCCTCTTGCTTCT (SEQ ID NO: 25) | 57 |
| P53-8R | ATAACTGCACCCTTGGTCTC (SEQ ID NO: 26) | |
| P53-9F | GCGCG-GCAGTTATGCCTCAGATTCA (SEQ ID NO: 27) | 55 |
| P53-9R | CGCCCGCCGCGCCCCGCGCCCGTCCCGCCGCCCC CGCCCG-CCCAATTGCAGGTAAAACAG (SEQ ID NO: 28) | |

DGGE: denaturant gradient gel electrophoresis

TABLE 6

Germl, lne, RRCA1/2 and Somatic TP53 Mutations In Samples From Hereditary Breast And Ovarian Cancer (HBOC) Patients

| | | | Somatic TP53 mutation | |
|---|---|---|---|---|
| Fam | Sample ID | Germline BRCA mutation | Epithelium | Stroma |
| 1 | 1 | BRCA1 4020delAG | Pro89Ser 1612insA | Pro89Ser Arg273Cys |
| 2 | 2 | BRCA1 IVS4-1G > T | Pro89Ser | — |
| 3 | 3 | BRCA1 1135 insA | Pro89Ser | — |
| 4 | 4 | BRCA1 2530delAG | Pro89Ser | Pro89Ser |
| 5 | 5 | BRCA1 1240delC | Pro89Ser Arg273Cys | — |
| 6 | 6 | BRCA1 589delCT | Pro219Ser | — |
| 7 | 7 | BRCA1 IVS18 + 3A/C | — | Asp41Asn |
| 8 | 8 | BRCA1 1389insAG | — | codon209 delGA |
| 9 | 9 | BRCA1 IVS6-1C/T | Pro89Ser | Pro89Ser Asp184Asn |
| 10 | 10 | BRCA1 del ex23-24 | 1733insA | — |
| 11 | 11 | BRCA1 IVS18 + 3A/C | Thr170Met | — |
| 12 | 12 | BRCA1 del ex23-24 | — | — |
| 13 | 13 | BRCA1 157delCT | — | Thr150Ile |
| 14 | 14 | BRCA1 4229insATCT | Val157Ile Arg248Glu | Pro89Ser |
| 15 | 15 | BRCA1 5385insC | Arg273Cys | — |
| 16 | 16 | BRCA1 2552delC | — | — |
| 17 | 17 | BRCA1 C61G | Pro89Ser Ser149Phe | — |
| 18 | 18 | BRCA1 IVS5-11T > G | Arg248Glu | — |
| 19 | 19 | BRCA1 + BRCA2 A1708E + 8234delTT | Ala88Thr Glu144Arg | — |
| | 20 | BRCA2 6503delTT | — | — |
| 20 | 21 | BRCA2 6503delTT | — | Glu198Lys |
| 21 | 22 | BRCA2 2567delC | Pro89Ser | Pro89Ser Arg273Cys |
| 22 | 23 | BRCA2 Y1894X | — | — |
| 23 | 24 | BRCA2 5578delAA | — | — |
| 24 | 25 | BRCA2 8234del23 | Pro177Arg Glu221Lys | — |
| 25 | 26 | BRCA2 5804delAAAA | — | Glu198Lys |
| 26 | 27 | BRCA2 3036delACAA | — | — |
| 27 | 28 | BRCA2 8294insTT | — | Pro89Ser |
| 28 | 29 | BRCA1uv S1040N | Pro89Ser | — |

TABLE 6-continued

Germline, RRCA1/2 and Somatic TP53 Mutations In Samples From
Hereditary Breast And Ovarian Cancer (HBOC) Patients

| Fam | Sample ID | Germline BRCA mutation | | Somatic TP53 mutation Epithelium | Stroma |
|---|---|---|---|---|---|
| 29 | 30 | BRCA1uv | S1040N | — | — |
| 30 | 31 | BRCA1uv | N1236K | — | Ser313Asn |
| 31 | 32 | BRCA1luv | A1623G | — | — |
|  | 33 | BRCA1uv | S1623G | — | Pro177Ser |
| 32 | 34 | BRCA1uv | IVS2-14T > C | — | Asp184Asn |
| 33 | 35 | BRCA2uv | I3412V | — | Pro89Ser |
|  |  |  |  |  | His179Arg |
| 34 | 36 | BRCA2uv | K1057R | Pro89Ser | Ala161Thr |
|  |  |  |  | Thr140Ala | Asp186Gly |
| 35 | 37 | BRCA2uv | A2466V | — | — |
| 36 | 38 | BRCA2uv | IVS8 + 56T > C | Ala161Val | Arg174Gly |
| 37 | 39 | BRCA2uv | A2951T | Thr170Ala Glu180Gly | Pro152Ser |
| 38 | 40 | BRCA2uv | A2951T | — | Met133Val |
| 39 | 41 | BRCA2uv | IVS21-11A/C | Pro89Ser ivs8 + 1 G/T | Pro89Ser |
|  | 42 | wt |  | Pro89Ser Asp324His | Pro89Ser |
| 40 | 43 | wt |  | — | — |

TABLE 7

Somatic Mutations of TP53 In Epithelial And Stromal DNA In
Sporadic Breast Cancer Patients

| Sample ID | Somatic TP53 mutation Epithelium | Stroma |
|---|---|---|
| 1 | Del1 bp codon 171 | — |
| 2 | Pro89Ser | — |
| 3 | delT codon275 | — |
| 4 | Arg196X | — |
| 5 | His296Tyr | — |
| 6 | Val173Met | — |
| 7 | Arg214X | — |
| 8 | Gly245Ser | — |
| 9 | Pro152Leu, Arg158Cys | — |
| 10 | Arg213X | — |
| 11 | 393insC | — |
| 12 | Arg273Cys | — |
| 13 | Ile195Thr | — |
| 14 | Arg209Lys | — |
| 15 | His179Asp | — |
| 16 | Cys176Trp | — |
| 17 | Arg282Gly | — |
| 18 | Arg156His, Pro177Ser | — |
| 19 | His178Tyr | — |
| 20 | Val172Ile | — |
| 21 | 532delC | — |
| 22 | Leu137Pro, Val172Ala | — |
| 23 | Asp184Gly | — |
| 24 | Pro98Leu, His168Tyr | — |
| 25 | Gln136Arg | — |
| 26 | Trp146Arg, Pro316Leu | — |
| 27 | — | Pro177Leu |
| 28 | — | Glu198Lys |
| 29 | — | His168Tyr |
| 30 | — | Cys182Arg |
| 31 | — | Val157Asp |
| 32 | — | Leu188Pro, Glu198Lys |
| 33 | — | Phe270Leu |
| 34 | — | Cys277Gly |
| 35 | — | Arg158Ser |
| 36 | — | Ala159Pro |
| 37 | — | Ala159Pro |
| 38 | — | Arg213X |
| 39 | — | Thr155Ala, Thr155Ile |
| 40 | — | Met133Val, His178Arg |
| 41 | — | Arg213X |
| 42 | — | Pro151Ser |
| 43 | — | Thr155Ile |
| 44 | — | Val218Ala |
| 45 | — | Thr150Ile |
| 46 | — | Leu145Pro, Arg196X |
| 47 | — | Val173Ala |
| 48 | — | Glu198Lys |
| 49 | — | 532insC |
| 50 | — | Ser183Leu |
| 51 | — | Pro75Leu |
| 52 | — | Pro278Ser |
| 53 | — | Gly325Arg |
| 54 | — | Gly226Ser |
| 55 | — | Thr140Ile, 565delG |
| 56 | — | Asp210Ser |
| 57 | — | Gln167His |
| 58 | — | Gln136X, His214Tyr |
| 59 | — | Glu198Lys, Val218Ala |
| 60 | — | Ser149Phe, Pro153Ser |
| 61 | delG codon108 | Pro153Ser, Glu198Lys |
| 62 | 532delC | Arg174Gly, 599delA |
| 63 | Arg156Cys, 532delC | Gln165Arg |
| 64 | Glu198Lys, Arg273His | His296Leu, His297Tyr |
| 65 | Gln136Arg | Arg290Gln |
| 66 | Ala161Val, Pro316Leu | Gly279Glu |
| 67 | Ala138Thr, Ser149Ala | Thr170Ala, Thr170Met |
| 68 | Asp184Asn | Gly279Arg |
| 69 | Ser166Leu, Cys176Ser | Arg175Cys |
| 70 | Arg213Glu | Arg213Glu |
| 71 | Tyr236Cys | Arg174Gly, Cys176Tyr |
| 72 | Ser183Leu | Arg280Ser |
| 73 | Phe134Cys | Thr155Ser |
| 74 | Arg181Cys | Arg273Cys |

TABLE 8

Mutated TP53-Associated Markers in Both Epithelium and Stroma of Sporadic Breast Cancer.

| Loci | Marker | LOH frequency (Epithelium) | P value* | LOH frequency (Stroma) | P value* | Gene(s) |
|---|---|---|---|---|---|---|
| 2q34 | D2S2944 | 18/29 (0.62) | 0.010 | 22/32 (0.69) | 0.021 | SPAG16 |
| 3q27.3 | D3S1262 | 18/28 (0.64) | <.001 | 18/24 (0.79) | <.001 | TP73L, SST, SENP2, MAP3K13 |
| 5q15 | D5S1462 | 22/27 (0.81) | <.001 | 21/29 (0.72) | 0.005 | LNPEP, LIX1, RIOK2 |
| 7p12.3 | D7S1818 | 16/19 (0.84) | 0.006 | 20/25 (0.80) | 0.005 | ABC13 |
| 15q11.2 | D15S128 | 17/22 (0.77) | 0.002 | 14/21 (0.67) | 0.009 | SNORD107 |
| 16p13 | D16S2616 | 18/29 (0.62) | 0.014 | 20/30 (0.67) | 0.004 | MYLE, SOCS1, TNP2 |
| 18q23 | D18S1390 | 14/22 (0.64) | 0.011 | 19/28 (0.68) | 0.001 | PARD6G, TXNL4A |
| 20p13 | D20S103 | 15/28 (0.54) | 0.021 | 17/32 (0.53) | 0.005 | CSNK2A1, TCF15, SCRT2 |

*Multiple testing adjustment is based on false-positive report probability $FPRP_{0.01} < 0.5$

TABLE 9

Hotspots of LOH/AI Associated With Mutated TP53 in Either Epithelium or Stroma of Breast Cancer

| Loci† | Marker | LOH frequency (Mutated TP53) | LOH frequency (Wild-type TP53) | P value* | Gene(s) |
|---|---|---|---|---|---|
| Sporadic Breast Cancer Samples Epithelium | | | | | |
| 5q35.1 | D5S1456 | 21/25 (0.84) | 34/82 (0.41) | <.001 | STK10, DRD1, FGFR4, MGAT1, MAPK9 |
| 8q22 | GAAT1A4 | 24/26 (0.92) | 46/89 (0.52) | <.001 | STK3, COX6C, POLR2K, TIEG, PPM2C, POP1, TP53INP1 |
| 16p12 | D16S403 | 18/32 (0.56) | 25/103 (0.24) | 0.002 | OLR3E, NDUFAB1 |
| 22q11.2 | D22S345 | 20/29 (0.69) | 25/78 (0.32) | 0.001 | CABIN |
| Stroma | | | | | |
| 7q21.3 | D7S821 | 21/26 (0.81) | 31/75 (0.41) | 0.001 | SHFM1, SLC25A13 |
| 8q24.13 | D8S1179 | 17/21 (0.81) | 28/71 (0.39) | 0.002 | FBOX032, ANXA13 |
| 11p15.5 | D11S1984 | 23/32 (0.72) | 30/82 (0.37) | 0.001 | COX8B, STK29, DUSP8, IGF2, INS, TH, SYT8 |
| 12q21 | D12S1052 | 19/25 (0.76) | 21/73 (0.29) | <.001 | CAPS2, RAB21, THAP2, PPP1R12A |
| 13q32.3 | D13S779 | 15/17 (0.88) | 14/51 (0.27) | <.001 | FGF14, VGCNL1 |
| 18q21.32 | D18S1357 | 20/26 (0.77) | 26/68 (0.38) | 0.002 | BCL2, DCC |
| HBOC samples Stroma | | | | | |
| 2p25.1 | D2S1400 | 14/18 (0.78) | 4/17 (0.23) | <.001 | E2F6, ROCK2 |

LOH: loss of heterozygosity;
HBOC: hereditary breast/ovarian cancer
*Multiple testing adjustment is based on false-positive report probability $FPRP_{0.01} < 0.5$
†Highest ranked markers; P < 0.005 (Tables 10-11).

TABLE 10

Mutated TP53 Associated LOH/AI Hotspot Markers in Sporadic Breast Cancer
Epithelium

| Loci | Marker | LOH frequency (TP53-Mutated) | LOH frequency (TP53-Wild type) | P value* | Gene(s) |
|---|---|---|---|---|---|
| Epithelium | | | | | |
| 1q23.1 | D1S1653 | 18/27 (0.67) | 29/80 (0.36) | 0.011 | CD cluster |
| 2p13 | D2S1394 | 19/27 (0.70) | 37/98 (0.38) | 0.005 | SPR, EMX1, SFXN5 |
| 2p25 | D2S1400 | 16/26 (0.62) | 26/82 (0.32) | 0.012 | E2F6, ROCK2 |
| 2p14 | D2S441 | 18/25 (0.72) | 37/89 (0.42) | 0.013 | PPP3R1, PN01 |
| 4q23 | D4S1647 | 18/26 (0.69) | 41/98 (0.42) | 0.023 | TSPAN5, BTF3L3, RAP1GDS1 |
| 5q35.1 | D5S1456 | 21/25 (0.84) | 34/82 (0.41) | <.001 | STK10, DRD1, FGFR4, MGAT1, MAPK9 |
| 5q14 | D5S1725 | 18/26 (0.69) | 33/83 (0.40) | 0.016 | — |
| 6q24.3 | GATA184A08 | 18/25 (0.72) | 33/80 (0.41) | 0.014 | — |
| 8q22 | GATT1A4 | 24/26 (0.92) | 46/89 (0.52) | <.001 | STK3, COX6C, POLR2K, TIEG, PPM2C, POP1, TP53INP1 |
| 8q24.3 | D8S373 | 15/20 (0.75) | 29/76 (0.38) | 0.007 | GLI4, LY6H, MAFA |
| 12q12 | D12S1301 | 18/25 (0.72) | 37/94 (0.39) | 0.007 | IRAK4, PUS7L |
| 12q24 | D12S1045 | 19/34 (0.56) | 31/98 (0.32) | 0.021 | TMEM132D, FZD10 |
| 12q21 | D12S1064 | 19/27 (0.70) | 37/88 (0.42) | 0.018 | — |
| 14q32.2 | D14S1426 | 20/28 (0.71) | 39/98 (0.41) | 0.007 | DEGS2, EVL, YY1 |
| 15q22.2 | D15S643 | 20/26 (0.77) | 44/95 (0.46) | 0.010 | LDHAL6B, FAM81A |
| 15q13.3 | D15S165 | 18/22 (0.82) | 23/49 (0.47) | 0.012 | KIAA1018, MTMR10, TRPM1 |
| 16p12 | D16S403 | 18/32 (0.56) | 25/103 (0.24) | 0.001 | POLR3E, NDUFAB1 |
| 17q21.31 | D17S579 | 18/25 (0.72) | 33/77 (0.43) | 0.014 | DBF4B, CCDC43, ADAM11 |
| 17q21.32 | D17S2180 | 17/25 (0.68) | 36/90 (0.40) | 0.024 | HOX cluster |
| 18q22.3 | ATA82B02 | 22/29 (0.76) | 40/88 (0.45) | 0.008 | — |
| 18q12.3 | D18S535 | 21/32 (0.66) | 34/90 (0.38) | 0.012 | — |
| 20p13 | D20S482 | 20/31 (0.65) | 36/96 (0.38) | 0.015 | RASSF2, ADRA1D |
| 22q11.2 | D22S345 | 20/29 (0.69) | 25/78 (0.32) | 0.001 | CABIN |
| 22q11.2 | D22S1045 | 20/24 (0.83) | 36/77 (0.47) | 0.003 | SSTR3, COX5BL7, BIK |
| Xq25 | GATA165B12 | 18/22 (0.82) | 36/82 (0.44) | 0.003 | NKAP, NDUFA |

LOH: loss of heterozygosity;
HBOC: hereditary breast ovary cancer
*Multiple testing adjustment is based on false-positive report probability $FPRP_{0.01} < 0.5$

TABLE 11

Mutated TP53 Associated LOH/AI Hotspot Markers in Sporadic Breast Cancer.
Stroma

| Loci | Marker | LOH frequency (TP53-Mutated) | LOH frequency (TP53-Wild type) | P value* | Gene(s) |
|---|---|---|---|---|---|
| Stroma | | | | | |
| 1p34.2 | D1S3721 | 19/25 (0.83) | 32/72 (0.44) | 0.003 | MED8, CITED4 |
| 1p21 | D1S1627 | 19/26 (0.73) | 30/76 (0.39) | 0.006 | — |
| 1p31 | D1S1596 | 17/28 (0.61) | 22/71 (0.31) | 0.012 | GBP cluster |
| 3p26.3 | D3S3630 | 18/24 (0.75) | 28/73 (0.38) | 0.003 | CNTN4 |
| 3p24.1 | D3S2432 | 19/27 (0.70) | 36/92 (0.39) | 0.008 | GPD1L |
| 3q24 | D3S1744 | 20/26 (0.77) | 34/83 (0.41) | 0.002 | CPB1 |
| 3q29 | D3S1311 | 16/27 (0.59) | 31/94 (0.33) | 0.024 | DLG1 |
| 3q28 | D3S2418 | 17/29 (0.59) | 26/79 (0.33) | 0.028 | FGF12 |
| 4q35.1 | D4S408 | 13/16 (0.81) | 22/55 (0.40) | 0.008 | ENPP6 |
| 7p21.3 | D7S3047 | 19/25 (0.76) | 36/78 (0.46) | 0.017 | — |

TABLE 11-continued

Mutated TP53 Associated LOH/AI Hotspot Markers in Sporadic Breast Cancer.
Stroma

| Loci | Marker | LOH frequency (TP53-Mutated) | LOH frequency (TP53-Wild type) | P value* | Gene(s) |
|---|---|---|---|---|---|
| 7q21.3 | D7S821 | 21/26 (0.81) | 31/75 (0.41) | 0.001 | SHFM1, SLC25A13 |
| 8q24.13 | D8S1179 | 17/21 (81.0) | 28/71 (39.4) | 0.002 | FBOX032, ANXA13 |
| 10p13 | D10S1430 | 16/23 (0.70) | 32/81 (0.40) | 0.020 | CAMK1D, CCDC3 |
| 10q23.3 | D10S677 | 21/30 (0.70) | 32/87 (0.37) | 0.003 | PLCE1, NOC3L |
| 10q24.3 | D10S1239 | 15/20 (0.75) | 25/67 (0.37) | 0.006 | BTRC, POLL |
| 11p15.5 | D11S1984 | 23/32 (71.9) | 30/82 (36.6) | 0.001 | COX8B, STK29, DUSP8, IGF2, INS, TH, SYT8 |
| 12p13 | D12S372 | 16/24 (0.67) | 24/71 (0.34) | 0.009 | TSPAN9, PRMT8 |
| 12q21 | D12S1052 | 19/25 (76.0) | 21/73 (28.8) | <.001 | CAPS2, RAB21, THAP2, PPP1R12A |
| 12q23 | PAH | 14/18 (0.78) | 19/57 (0.33) | 0.002 | PAH, ASCL1 |
| 13q32.3 | D13S779 | 15/17 (88.2) | 14/51 (27.4) | <.001 | FGF14, VGCNL1 |
| 13q | ATA5A09 | 17/24 (0.71) | 32/84 (0.38) | 0.009 | — |
| 16p | D16S3401 | 17/26 (0.65) | 28/91 (0.31) | 0.003 | — |
| 16q24 | D16S413 | 20/25 (0.80) | 35/77 (0.45) | 0.005 | SLC7A5, CA5A |
| 17p13.1 | D17S974 | 9/12 (0.75) | 18/62 (0.29) | 0.006 | MYH cluster, SCO1 |
| 17q24.2 | D17S2193 | 17/24 (0.71) | 30/74 (0.41) | 0.019 | PRKAR1A |
| 18p11 | D18S843 | 17/24 (0.71) | 28/74 (0.38) | 0.009 | RAB12 |
| 18q21.32 | D18S1357 | 20/26 (76.9) | 26/68 (38.2) | 0.007 | BCL2, DCC |
| 18q12.1 | D18S887 | 17/23 (0.74) | 26/69 (0.38) | 0.005 | — |
| 22q11 | D22S686 | 20/27 (0.74) | 14/38 (0.37) | 0.006 | IGLV4-3 |
| 22q13.31 | D22S532 | 17/25 (0.68) | 21/61 (0.34) | 0.009 | ATXN10, WNT7B |
| 22q | GATA198B05 | 20/33 (0.61) | 36/103 (0.35) | 0.016 | — |
| 22q13 | D22S1169 | 20/33 (0.61) | 34/95 (0.36) | 0.022 | — |
| Xq25 | DXS1047 | 16/22 (0.73) | 35/85 (0.41) | 0.016 | UTP14A, RAB33A, ELF4 |

LOH: loss of heterozygosity;
HBOC: hereditary breast ovary cancer
*Multiple testing adjustment is based on false-positive report probability $FPRP_{0.01} < 0.5$

TABLE 12

Association Between Somatic TP53 Mutation Status And Clinicopathological Features (CPF) in Epithelium And Stroma of Sporadic Breast Cancer Patients.

| CPF | Level | Epithelium | | | Stroma | | |
|---|---|---|---|---|---|---|---|
| | | Mutated TP53 (N) | Wildtype TP53 (N) | P value* Odds Ratio (95% CI)‡ | Mutated TP53 (N) | Wildtype TP53 (N) | P value* Odds Ratio (95% CI)‡ |
| Grade (Tumor Stage) | | | | 0.99 | | | 0.08 |
| | 1 | 3 | 9 | | 2 | 10 | |
| | 2 | 19 | 63 | 2 vs 1 0.91 (0.22, 3.68) | 29 | 53 | 2 vs 1 2.74 (0.56, 13.34) |
| | 3 | 18 | 59 | 3 vs 1 0.92 (0.22, 3.75) | 16 | 61 | 3 vs 1 1.31 (0.26, 6.59) |
| Estrogen_Receptor | | | | 0.29 | | | 0.87 |
| | 0 | 15 | 39 | | 13 | 41 | |
| | 1 | 20 | 79 | 1 vs 0 0.66 (0.30, 1.42) | 25 | 74 | 1 vs 0 1.07 (0.49, 2.30) |
| Progesterone_Receptor | | | | 0.64 | | | 0.44 |
| | 0 | 14 | 40 | | 12 | 42 | |
| | 1 | 20 | 69 | 1 vs 0 0.83 (0.38, 1.82) | 25 | 64 | 1 vs 0 1.37 (0.62, 3.02) |
| HER2_NEU | | | | 0.63 | | | 0.32 |
| | 0 | 28 | 89 | 1 vs 0 0.80 (0.31, 2.02) | 27 | 90 | 1 vs 0 153 (0.66, 3.52) |
| | 1 | 7 | 28 | | 11 | 24 | |

TABLE 12-continued

Association Between Somatic TP53 Mutation Status And Clinicopathological Features (CPF) in Epithelium And Stroma of Sporadic Breast Cancer Patients.

| CPF | Level | Epithelium | | | Stroma | | |
|---|---|---|---|---|---|---|---|
| | | Mutated TP53 (N) | Wildtype TP53 (N) | P value* Odds Ratio (95% CI)‡ | Mutated TP53 (N) | Wildtype TP53 (N) | P value* Odds Ratio (95% CI)‡ |
| pT (Tumor Size) | | | | 0.78** | | | 0.99** |
| | 1 | 15 | 50 | | 19 | 46 | |
| | 2 | 13 | 44 | 2 vs 1<br>0.99 (0.42, 2.30) | 16 | 41 | 2 vs 1<br>0.95 (0.43, 2.08) |
| | 3 | 3 | 5 | 3 vs 1<br>2.00 (0.43, 9.36) | 2 | 6 | 3 vs 1<br>0.81 (0.15, 4.36) |
| | 4 | 2 | 7 | 4 vs 1<br>0.95 (0.18, 5.08) | 2 | 7 | 4 vs 1<br>0.69 (0.13, 3.64) |
| pN (Nodal Status) | | | | 0.21† | | | 0.003† |
| | 0 | 12 | 47 | | 18 | 42 | |
| | 1 | 10 | 37 | 1 vs 0<br>1.06 (0.41, 2.72) | 7 | 40 | 1 vs 0<br>0.41 (0.15, 1.08) |
| | 2 | 5 | 8 | 2 vs 0<br>2.45 (0.68, 8.85) | 5 | 8 | 2 vs 0<br>1.46 (0.42, 5.07) |
| | 3 | 3 | 3 | 3 vs 0<br>3.92 (0.77, 21.9) | 5 | 1 | 3 vs 0<br>11.67 (1.27, 107.1) |

*Chi-square
†Fischer exact test
‡Odds ratio test: baseline is wildtype TP53 and the first level of each parameter.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention described herein.

What is claimed is:

1. A method of detecting increased likelihood of nodal metastasis of a breast tumor in a human subject in need thereof comprising detecting an increase in a loss of heterozygosity (LOH) or allelic imbalance (AI) at the following loci: D7S821, D10S677, D15S128, D16S3401, and D17S2193 in breast tumor stroma of the subject, wherein the increase of LOH or AI at the loci D7S821, D10S677, D15S128, D16S3401, and D17S2193 in the breast tumor stroma indicates increased likelihood of nodal metastasis of the breast tumor in the subject.

2. The method of claim 1, wherein the subject has sporadic breast cancer.

3. The method of claim 1, wherein the LOH or AI is detected by performing polymerase chain reaction (PCR) on DNA obtained from the breast tumor stroma.

4. The method of claim 3, wherein the LOH or AI is detected by PCR followed by gentoyping.

5. The method of claim 3, further comprising detecting a mutation of the TP53 gene, wherein the mutation of the TP53 gene is detected
by performing PCR amplification of exons 4 to 9 of the TP53 gene followed by denaturing gradient gel electrophoresis.

6. A method of diagnosing detecting increased likelihood of breast cancer in a human subject in need thereof comprising detecting an increase in a loss of heterozygosity (LOH) or allelic imbalance (AI) at the following loci D7S821, D10S677, D15S128, D16S3401, and D17S2193 in breast tumor stroma of the subject, wherein the increase of LOH or AI at the loci D7S821, D10S677, D15S128, D16S3401, and D17S2193 in the breast tumor stroma indicates increased likelihood a diagnosis of breast cancer in the subject.

7. The method of claim 6, wherein the subject has sporadic breast cancer.

8. The method of claim 6, further comprising detecting a mutation of the TP53 gene in breast tumor stroma of the subject.

9. The method of claim 8, wherein the mutation of the TP53 gene or the LOH or AI is detected by performing polymerase chain reaction (PCR) on DNA obtained from the breast tumor stroma.

10. The method of claim 6, wherein the LOH or AI is detected by performing polymerase chain reaction PCR on DNA obtained from the breast tumor stroma.

11. The method of claim 9, wherein the mutation of the TP53 gene is detected by performing PCR amplification of exons 4 to 9 of the TP53 gene followed by denaturing gradient gel electrophoresis.

12. The method of claim 10, wherein the LOH or AI is detected by PCR followed by genotyping.

13. The method of claim 1, further comprising detecting a mutation of the TP53 gene in breast tumor stroma of the subject.

* * * * *

SEQUENCE LISTING

```
<160> NUMBER OF SEQ ID NOS: 34

<210> SEQ ID NO 1
<211> LENGTH: 29
<212> TYPE: DNA
<213> ORGANISM: Unknown
<220> FEATURE:
<223> OTHER INFORMATION: P53-4F sequence, forward primer used for
      sequencing of TP53

<400> SEQUENCE: 1
cctggtcctc tgactgctct tttcaccca                                    29

<210> SEQ ID NO 2
<211> LENGTH: 21
<212> TYPE: DNA
<213> ORGANISM: Unknown
<220> FEATURE:
<223> OTHER INFORMATION: P53-4R sequence, reverse primer used for
      sequencing of TP53

<400> SEQUENCE: 2
ggccaggcat tgaagtctca t                                            21

<210> SEQ ID NO 3
<211> LENGTH: 18
<212> TYPE: DNA
<213> ORGANISM: Unknown
<220> FEATURE:
<223> OTHER INFORMATION: P53-5F sequence, forward primer used for
      sequencing of TP53

<400> SEQUENCE: 3
```

```
caactctgtc tccttcct                                              18
```

<210> SEQ ID NO 4
<211> LENGTH: 18
<212> TYPE: DNA
<213> ORGANISM: Unknown
<220> FEATURE:
<223> OTHER INFORMATION: P53-5R sequence, reverse primer used for
      sequencing of TP53

<400> SEQUENCE: 4

```
tgtcgtctct ccagcccc                                              18
```

<210> SEQ ID NO 5
<211> LENGTH: 20
<212> TYPE: DNA
<213> ORGANISM: Unknown
<220> FEATURE:
<223> OTHER INFORMATION: P53-6F sequence, forward primer used for
      sequencing of TP53

<400> SEQUENCE: 5

```
agagacgaca gggctggttg                                            20
```

<210> SEQ ID NO 6
<211> LENGTH: 20
<212> TYPE: DNA
<213> ORGANISM: Unknown
<220> FEATURE:
<223> OTHER INFORMATION: P53-6R sequence, reverse primer used for
      sequencing of TP53

<400> SEQUENCE: 6

```
cttaacccct cctcccagag                                            20
```

<210> SEQ ID NO 7
<211> LENGTH: 20
<212> TYPE: DNA
<213> ORGANISM: Unknown
<220> FEATURE:
<223> OTHER INFORMATION: P53-7F sequence, forward primer used for
      sequencing of TP53

<400> SEQUENCE: 7

```
cctcatcttg ggcctgtgtt                                            20
```

<210> SEQ ID NO 8
<211> LENGTH: 20
<212> TYPE: DNA
<213> ORGANISM: Unknown
<220> FEATURE:
<223> OTHER INFORMATION: P53-7R sequence, reverse primer used for
      sequencing of TP53

<400> SEQUENCE: 8

```
agtgtgcagg gtggcaagtg                                            20
```

<210> SEQ ID NO 9
<211> LENGTH: 20
<212> TYPE: DNA
<213> ORGANISM: Unknown
<220> FEATURE:
<223> OTHER INFORMATION: P53-8F sequence, forward primer used for
      sequencing of TP53

<400> SEQUENCE: 9

```
ccttactgcc tcttgcttct                                            20
```

```
<210> SEQ ID NO 10
<211> LENGTH: 20
<212> TYPE: DNA
<213> ORGANISM: Unknown
<220> FEATURE:
<223> OTHER INFORMATION: P53-8R sequence, reverse primer used for
      sequencing of TP53

<400> SEQUENCE: 10
ataactgcac ccttggtctc                                              20

<210> SEQ ID NO 11
<211> LENGTH: 28
<212> TYPE: DNA
<213> ORGANISM: Unknown
<220> FEATURE:
<223> OTHER INFORMATION: P53-9F sequence, forward primer used for
      sequencing of TP53

<400> SEQUENCE: 11
ggagaccaag ggtgcagtta tgcctcag                                     28

<210> SEQ ID NO 12
<211> LENGTH: 20
<212> TYPE: DNA
<213> ORGANISM: Unknown
<220> FEATURE:
<223> OTHER INFORMATION: P53-9R sequence, reverse primer used for
      sequencing of TP53

<400> SEQUENCE: 12
cccaattgca ggtaaaacag                                              20

<210> SEQ ID NO 13
<211> LENGTH: 28
<212> TYPE: DNA
<213> ORGANISM: Unknown
<220> FEATURE:
<223> OTHER INFORMATION: P53-4.1F, forward primer used for denaturant
      gradient gel electrophoresis of TP53

<400> SEQUENCE: 13
cgtcccgctg gtcctctgac tgctctttt                                    28

<210> SEQ ID NO 14
<211> LENGTH: 60
<212> TYPE: DNA
<213> ORGANISM: Unknown
<220> FEATURE:
<223> OTHER INFORMATION: P53-4.1R, reverse primer used for denaturant
      gradient gel electrophoresis of TP53

<400> SEQUENCE: 14
cgcccgccgc gccccgcgcc cgtcccgccg ccccgcccg cattctggga gcttcatctg    60

<210> SEQ ID NO 15
<211> LENGTH: 18
<212> TYPE: DNA
<213> ORGANISM: Unknown
<220> FEATURE:
<223> OTHER INFORMATION: P53-4.2F, forward primer used for denaturant
      gradient gel electrophoresis of TP53

<400> SEQUENCE: 15
aagctcccag aatgccag                                                18

<210> SEQ ID NO 16
```

```
<211> LENGTH: 68
<212> TYPE: DNA
<213> ORGANISM: Unknown
<220> FEATURE:
<223> OTHER INFORMATION: P53-4.2R, reverse primer used for denaturant
      gradient gel electrophoresis of TP53

<400> SEQUENCE: 16
cgcccgccgc cgcccgccgc gccccgcgcc cgtcccgccg ccccgcccg gcaagaagcc      60 cagacgga                                                             68

<210> SEQ ID NO 17
<211> LENGTH: 68
<212> TYPE: DNA
<213> ORGANISM: Unknown
<220> FEATURE:
<223> OTHER INFORMATION: P53-4.3F, forward primer used for denaturant
      gradient gel electrophoresis of TP53

<400> SEQUENCE: 17
cgcccgccgc cgcccgccgc gccccgcgcc cgtcccgccg ccccgcccg tccttccca      60 gaaaacct                                                             68

<210> SEQ ID NO 18
<211> LENGTH: 18
<212> TYPE: DNA
<213> ORGANISM: Unknown
<220> FEATURE:
<223> OTHER INFORMATION: P53-4.3R, reverse primer used for denaturant
      gradient gel electrophoresis of TP53

<400> SEQUENCE: 18
tgaagtctca tggaagcc                                                  18

<210> SEQ ID NO 19
<211> LENGTH: 68
<212> TYPE: DNA
<213> ORGANISM: Unknown
<220> FEATURE:
<223> OTHER INFORMATION: P53-5F, forward primer used for denaturant
      gradient gel electrophoresis of TP53

<400> SEQUENCE: 19
cgcccgccgc cgcccgccgc gccccgcgcc cgtcccgccg ccccgcccg caactctgtc      60 tccttcct                                                             68

<210> SEQ ID NO 20
<211> LENGTH: 18
<212> TYPE: DNA
<213> ORGANISM: Unknown
<220> FEATURE:
<223> OTHER INFORMATION: P53-5R, reverse primer used for denaturant
      gradient gel electrophoresis of TP53

<400> SEQUENCE: 20
tgtcgtctct ccagcccc                                                  18

<210> SEQ ID NO 21
<211> LENGTH: 20
<212> TYPE: DNA
<213> ORGANISM: Unknown
<220> FEATURE:
<223> OTHER INFORMATION: P53-6F, forward primer used for denaturant
      gradient gel electrophoresis of TP53

<400> SEQUENCE: 21
```
agagacgaca gggctggttg                                               20

<210> SEQ ID NO 22
<211> LENGTH: 70
<212> TYPE: DNA
<213> ORGANISM: Unknown
<220> FEATURE:
<223> OTHER INFORMATION: P53-6R, reverse primer used for denaturant
      gradient gel electrophoresis of TP53

<400> SEQUENCE: 22
cgcccgccgc gccccgcgcc cggcccgccg ccccgcccg aaataataaa ccttaacccc    60
tcctcccaga                                                          70

<210> SEQ ID NO 23
<211> LENGTH: 60
<212> TYPE: DNA
<213> ORGANISM: Unknown
<220> FEATURE:
<223> OTHER INFORMATION: P53-7F, forward primer used for denaturant
      gradient gel electrophoresis of TP53

<400> SEQUENCE: 23
cgcccgccgc gccccgcgcc cgtcccgccg ccccgcccg cctcatcttg ggcctgtgtt    60

<210> SEQ ID NO 24
<211> LENGTH: 20
<212> TYPE: DNA
<213> ORGANISM: Unknown
<220> FEATURE:
<223> OTHER INFORMATION: TP53-7R, reverse primer used for denaturant
      gradient gel electrophoresis of TP53

<400> SEQUENCE: 24
agtgtgcagg gtggcaagtg                                               20

<210> SEQ ID NO 25
<211> LENGTH: 60
<212> TYPE: DNA
<213> ORGANISM: Unknown
<220> FEATURE:
<223> OTHER INFORMATION: P53-8F, forward primer used for denaturant
      gradient gel electrophoresis of TP53

<400> SEQUENCE: 25
cgcccgccgc gccccgcgcc cgtcccgccg ccccgcccg ccttactgcc tcttgcttct    60

<210> SEQ ID NO 26
<211> LENGTH: 20
<212> TYPE: DNA
<213> ORGANISM: Unknown
<220> FEATURE:
<223> OTHER INFORMATION: P53-8R, reverse primer used for denaturant
      gradient gel electrophoresis of TP53

<400> SEQUENCE: 26
ataactgcac ccttggtctc                                               20

<210> SEQ ID NO 27
<211> LENGTH: 25
<212> TYPE: DNA
<213> ORGANISM: Unknown
<220> FEATURE:
<223> OTHER INFORMATION: P53-9F, forward primer used for denaturant
      gradient gel electrophoresis of TP53

<400> SEQUENCE: 27

```
gcgcggcagt tatgcctcag attca                                           25
```

<210> SEQ ID NO 28
<211> LENGTH: 60
<212> TYPE: DNA
<213> ORGANISM: Unknown
<220> FEATURE:
<223> OTHER INFORMATION: P53-9R, reverse primer used for denaturant
      gradient gel electrophoresis of TP53

<400> SEQUENCE: 28

```
cgcccgccgc gccccgcgcc cgtcccgccg ccccogcccg cccaattgca ggtaaaacag      60
```

<210> SEQ ID NO 29
<211> LENGTH: 22
<212> TYPE: DNA
<213> ORGANISM: Unknown
<220> FEATURE:
<223> OTHER INFORMATION: TP53 Normal Tissue (Wild typy (Val173Val))

<400> SEQUENCE: 29

```
acggaggttg tgaggcgctg cc                                              22
```

<210> SEQ ID NO 30
<211> LENGTH: 22
<212> TYPE: DNA
<213> ORGANISM: Unknown
<220> FEATURE:
<223> OTHER INFORMATION: TP53 Breast-Cancer (Stroma mutant (Val173Ala))

<400> SEQUENCE: 30

```
acggaggttg cgaggcgctg cc                                              22
```

<210> SEQ ID NO 31
<211> LENGTH: 14
<212> TYPE: DNA
<213> ORGANISM: Unknown
<220> FEATURE:
<223> OTHER INFORMATION: TP53 (NC_000017)

<400> SEQUENCE: 31

```
ctggatggag aata                                                       14
```

<210> SEQ ID NO 32
<211> LENGTH: 14
<212> TYPE: DNA
<213> ORGANISM: Unknown
<220> FEATURE:
<223> OTHER INFORMATION: TP53 (NC_000017)

<400> SEQUENCE: 32

```
ctggatagag aata                                                       14
```

<210> SEQ ID NO 33
<211> LENGTH: 5
<212> TYPE: PRT
<213> ORGANISM: Unknown
<220> FEATURE:
<223> OTHER INFORMATION: P53 protein

<400> SEQUENCE: 33

Leu Asp Gly Glu Tyr
 1               5

<210> SEQ ID NO 34
<211> LENGTH: 5
<212> TYPE: PRT

```
<213> ORGANISM: Unknown
<220> FEATURE:
<223> OTHER INFORMATION: P53 protein

<400> SEQUENCE: 34

Leu Asp Arg Glu Tyr
 1               5
```